United States Patent
Song et al.

(10) Patent No.: US 11,990,206 B2
(45) Date of Patent: May 21, 2024

(54) METHODS FOR DETECTING VARIANTS IN NEXT-GENERATION SEQUENCING GENOMIC DATA

(71) Applicant: SOPHIA GENETICS S.A., Saint Sulpice (CH)

(72) Inventors: Lin Song, Saint Sulpice (CH); Zhenyu Xu, Commugny (CH)

(73) Assignee: SOPHIA GENETICS S.A., Rolle (CH)

( * ) Notice: Subject to any disclaimer, the term of this patent is extended or adjusted under 35 U.S.C. 154(b) by 1263 days.

(21) Appl. No.: 16/467,265

(22) PCT Filed: Dec. 7, 2017

(86) PCT No.: PCT/EP2017/081863
§ 371 (c)(1),
(2) Date: Jun. 6, 2019

(87) PCT Pub. No.: WO2018/104466
PCT Pub. Date: Jun. 14, 2018

(65) Prior Publication Data
US 2019/0311779 A1 Oct. 10, 2019

(30) Foreign Application Priority Data
Dec. 7, 2016 (EP) .................... 16202691

(51) Int. Cl.
*G16B 30/00* (2019.01)
*G06F 17/18* (2006.01)
(Continued)

(52) U.S. Cl.
CPC ............. *G16B 30/00* (2019.02); *G06F 17/18* (2013.01); *G16B 20/00* (2019.02); *G16B 20/20* (2019.02); *G16B 20/30* (2019.02); *G16B 30/10* (2019.02)

(58) Field of Classification Search
CPC ........ G16B 20/30; G16B 30/10; G16B 20/20; G16B 20/00; G06F 17/18
See application file for complete search history.

(56) References Cited

U.S. PATENT DOCUMENTS

| | | |
|---|---|---|
| 8,262,900 B2 | 9/2012 | Rothberg |
| 2009/0026082 A1 | 1/2009 | Rothberg |
| 2014/0052381 A1 | 2/2014 | Utiramerur |

OTHER PUBLICATIONS

Parmigiani, Giovanni, Donald A. Berry, and Omar Aguilar. "Determining carrier probabilities for breast cancer-susceptibility genes BRCA1 and BRCA2." The American Journal of Human Genetics 62.1 (1998): 145-158. (Year: 1998).*

(Continued)

*Primary Examiner* — Russell S Negin
*Assistant Examiner* — Guozhen Liu
(74) *Attorney, Agent, or Firm* — Bochner PLLC; Andrew D. Bochner

(57) ABSTRACT

A genomic data analyzer may be configured to detect and characterize, with a variant calling module, genomic variant scenarios in sequencing reads from an enriched patient genomic sample comprising a combination of a first repeat pattern and a second repeat pattern, such as repeats of homopolymer (single nucleotide) and/or heteropolymer (multiple nucleotide) basic motifs. The variant calling module may estimate the probability distribution of the length of the first repeat pattern and the probability distribution of the length of the second repeat pattern by comparing the distribution of the repeat pattern length measurements in patient data to the distribution of the repeat pattern length measurements in control data, in order to remove biases possibly induced by the next generation sequencing laboratory setup both in control and patient data. The variant calling module may further measure, read by read, the joint probability distribution for the first and the second repeat patterns (Continued)

lengths, and compare it with the expected joint probability distribution for various genomic variant scenarios for the patient, each variant scenario being characterized by a first length of the first repeat pattern and a second length of the second repeat pattern, to select the most likely patient genomic variant scenario as the scenario for which the measured joint probability distribution best matches the expected joint probability distribution.

13 Claims, 14 Drawing Sheets

(51) Int. Cl.
*G16B 20/00* (2019.01)
*G16B 20/20* (2019.01)
*G16B 20/30* (2019.01)
*G16B 30/10* (2019.01)

(56) References Cited

OTHER PUBLICATIONS

Xiao, Lihua. "Molecular epidemiology of cryptosporidiosis: an update." Experimental parasitology 124.1 (2010): 80-89. (Year: 2010).*
PCT Search Report and IPER issued in PCT/EP2017/081863.
Article cited in IPER XP055094485 dated Mar. 9, 2004.
Article cited in IPER XP055283052 dated Jul. 1, 2013.
Article cited in IPER XP021111527 dated Dec. 14, 2011.

* cited by examiner

```
Ref:     TGTGTGTG......TGTGTTTTTTT
Read1:   TGTGTG--......TGTGTT-TTTT
Read2:   TGTGTGTG......-TGTTTT-TTT
Read3:   TGTGTG--......TGTGT-TTTTT
Read4:   TG--TGTG......TGTGTTTT-T
Read5:   TGTGTG--......TGTGTTT-TTT
Read6:   TGTGTGTG......TG--TTT-TTT
Read7:   TGTGTGTG......--TGTTTTT-T
Read8:   TGTGTG--......TGTGTTTTT-T
Read9:   TGTG--TG......TGTGT-TTTTT
Read10:  TGTG--TG......TGTGT-TTTTT
Read11:  TG--TGTG......TGTGTTT-TTT
Read12:  TG--TGTG......TGTGTTTTTT-
Read13:  TGTGTGTG......TG--TTTT-TT
Read14:  TGTGTGTG......--TGTTT-TTT
Read15:  TGTGTGTG......--TGTT-TTTT
```

FIG.3

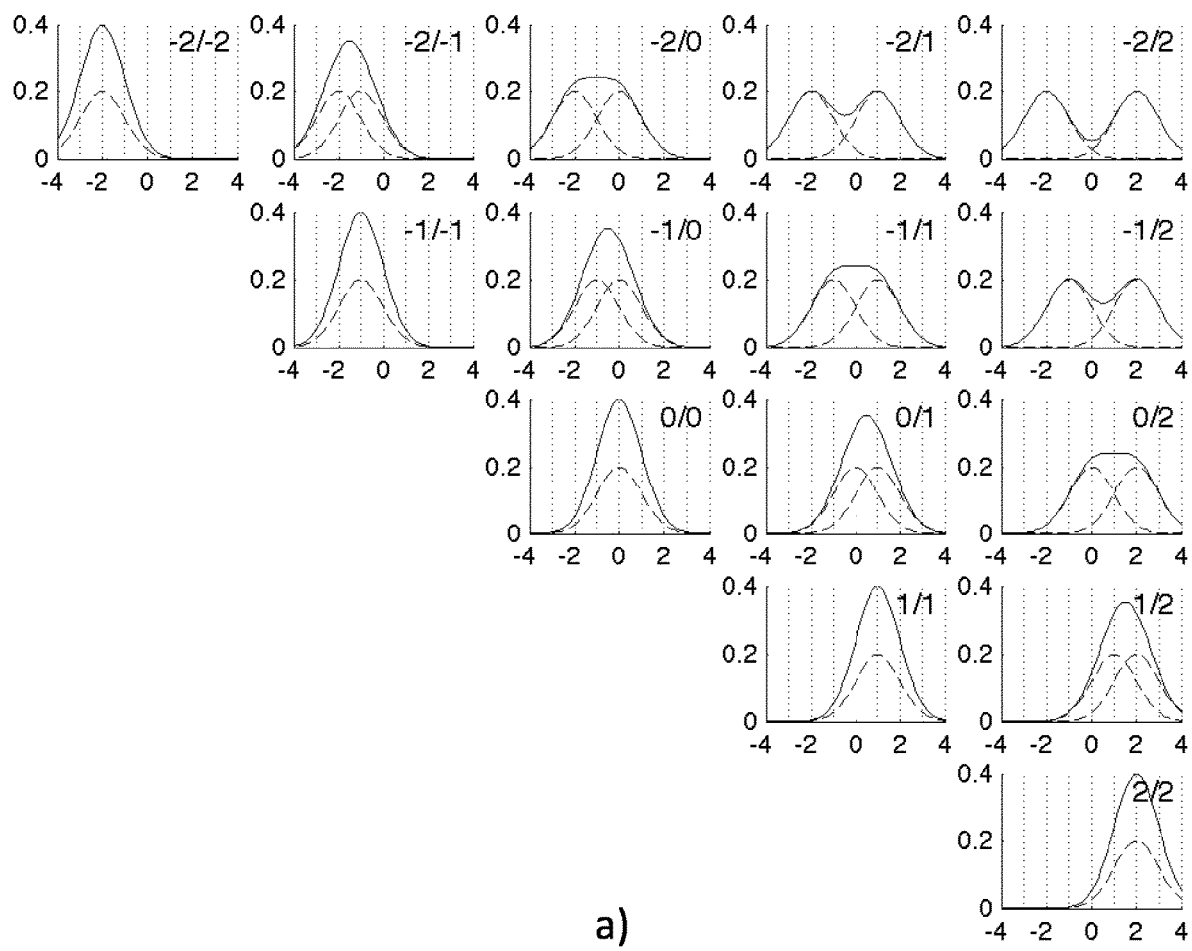
a)
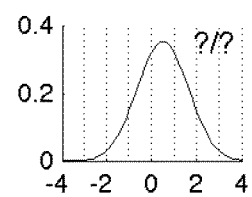
b)
FIG.7

```
Allele 1:  TGTGTGTGTGTGTGTGTGTGTGTGTTTTT
Allele 2:  TGTGTGTGTGTGTGTGTG------TTTTTTT
 Ref:      TGTGTGTGTGTGTGTGTGTG--TTTTTTT
``` a)

```
Allele 1:  TGTGTGTGTGTGTGTGTGTGTGTGTTTTTTT
Allele 2:  TGTGTGTGTGTGTGTGTG----------TTTTT
 Ref:      TGTGTGTGTGTGTGTGTGTG----TTTTTTT
``` b)

FIG.8

| TG\TT | -4 | -3 | -2 | -1 | 0 | +1 | +2 | +3 | +4 |
|---|---|---|---|---|---|---|---|---|---|
| -4 | 0 | 0 | 0 | 1 | 3 | 1 | 0 | 0 | 0 |
| -3 | 0 | 0 | 1 | 2 | 6 | 1 | 0 | 0 | 0 |
| -2 | 0 | 0 | 3 | 6 | 18 | 3 | 0 | 0 | 0 |
| -1 | 0 | 0 | 1 | 1 | 3 | 0 | 0 | 0 | 0 |
| 0 | 1 | 1 | 3 | 0 | 0 | 0 | 0 | 0 | 0 |
| +1 | 1 | 2 | 6 | 1 | 0 | 0 | 0 | 0 | 0 |
| +2 | 3 | 6 | 18 | 3 | 0 | 0 | 0 | 0 | 0 |
| +3 | 0 | 1 | 3 | 1 | 0 | 0 | 0 | 0 | 0 |
| +4 | 0 | 0 | 0 | 0 | 0 | 0 | 0 | 0 | 0 |

FIG.9a)

| TG\TT | -4 | -3 | -2 | -1 | 0 | +1 | +2 | +3 | +4 |
|---|---|---|---|---|---|---|---|---|---|
| -4 | 1 | 1 | 3 | 0 | 0 | 0 | 0 | 0 | 0 |
| -3 | 1 | 2 | 6 | 1 | 0 | 0 | 0 | 0 | 0 |
| -2 | 3 | 6 | 18 | 3 | 0 | 0 | 0 | 0 | 0 |
| -1 | 0 | 1 | 3 | 1 | 0 | 0 | 0 | 0 | 0 |
| 0 | 0 | 0 | 0 | 1 | 3 | 1 | 0 | 0 | 0 |
| +1 | 0 | 0 | 1 | 2 | 6 | 1 | 0 | 0 | 0 |
| +2 | 0 | 0 | 3 | 6 | 18 | 3 | 0 | 0 | 0 |
| +3 | 0 | 0 | 1 | 1 | 3 | 0 | 0 | 0 | 0 |
| +4 | 0 | 0 | 0 | 0 | 0 | 0 | 0 | 0 | 0 |

FIG.9b)

METHODS FOR DETECTING VARIANTS IN NEXT-GENERATION SEQUENCING GENOMIC DATA

FIELD OF THE INVENTION

Methods described herein relate to genomic analysis in general, and more specifically to next generation sequencing applications.

BACKGROUND OF THE INVENTION

Next-Generation Sequencing

High throughput next-generation sequencing (NGS) or massively parallel sequencing (MPS) technologies have significantly decreased the cost of DNA sequencing in the past decade. NGS has broad application in biology and dramatically changed the way of research or diagnosis methodologies. For example, RNA expression profiling or DNA sequencing can only be conducted with a few numbers of genes with traditional methods, such as quantitative PCR or Sanger sequencing. Even with microarrays, profiling the gene expression or identifying the mutation at the whole genome level can only be implemented for organisms whose genome size is relatively small. With NGS technology, RNA profiling or whole genome sequencing has become a routine practice now in biological research. On the other hand, due to the high throughput of NGS, multiplexed methods have been developed not just to sequence more regions but also to sequence more samples. Compared to the traditional Sanger sequencing technology, NGS enables the detection of mutation for much more samples in different genes in parallel. Due to its superiorities over traditional sequencing method, NGS sequencers are now replacing Sanger in routine diagnosis. In particular, genomic variations of individuals (germline) or of cancerous tissues (somatic) can now be routinely analyzed for a number of medical applications ranging from genetic disease diagnostic to pharmacogenomics fine-tuning of medication in precision medicine practice. NGS consists in processing multiple fragmented DNA sequence reads, typically short ones (less than 300 nucleotide base pairs). The resulting reads can then be compared to a reference genome by means of a number of bioinformatics methods, to identify small variants such as Single Nucleotide Polymorphisms (SNP) corresponding to a single nucleotide substitution, as well as short insertions and deletions (INDEL) of nucleotides in the DNA sequence compared to its reference.

Targeted Enrichment

In some pathologies, a specific gene variant has been associated with the illness, such as the BRCA1 and BRCA2 genes in certain forms of hereditary breast and ovarian cancers or the CFTR gene in cystic fibrosis. Rather than sequencing the whole genome (WGS) from an individual sample, the genomic analysis can focus on the genome region associated with the illness, by targeting, with a set of region-specific DNA primers or probes, and enriching or amplifying, for instance with PCR (Polymerase Chain Reaction), the biological DNA sample specifically for sub-regions corresponding to the gene along the DNA strand. A number of next generation sequencing assays have now been developed along those principles as ready-to-use biological kits, such as for instance the Multiplicom MASTR™ or the Illumina TruSeq® Amplicon assay kits to facilitate DNA based diagnostics with next generation sequencers, such as for instance the Illumina MiSeq® sequencer, in medical research and clinical practice.

Target enrichment may be achieved from a small sample of DNA by means of probe-based hybridization (on arrays or in-solution) or highly multiplexed PCR-based targeted exon enrichment, so that both the gene coverage/read depth and the amplification specificity (amplifying the right region, as measured by further alignment to the desired target regions) are maximized. Examples of commercially available target enrichment systems include Agilent SureSelect™ Target Enrichment System, Roche NimbleGen SeqCap EZ, Illumina Nextera Rapid Capture, Agilent Haloplex™, and Multiplicom MASTR™.

In order to maximize the use of the massively-parallel processing NGS sequencer, a number of samples are multiplexed in the targeted NGS experiment—a pool of 48 or more target enrichment samples can thus be simultaneously input to the Illumina MiSeq sequencer for instance. Raw sequencing data out of the NGS sequencer may then be analyzed to identify specific subsequences, for instance by alignment to a reference genome. As a result, the amplification may produce more than a thousand reads for a given amplicon in a patient sample.

Next Generation Sequencing Workflow Automation

Next Generation Sequencing (NGS) enables in particular to detect and report small changes in the DNA sequence, such as single nucleotide polymorphisms (SNPs), insertions or deletions (INDELs), as compared to the reference genome, through bioinformatics methods such as sequencing read alignment, variant calling, and variant annotation. NGS workflows refer to the configuration and combination of such methods into an end-to-end genomic analysis application. In genomic research practice, NGS workflows are often manually setup and optimized using for instance dedicated scripts on a UNIX operating system, dedicated platforms including a graphical pipeline representation such as the Galaxy project, and/or a combination thereof. As clinical practice develops, NGS workflows may no longer be experimentally setup on a case-per-case basis, but rather integrated in SaaS (Software as a Service), PaaS (Platform as a Service) or IaaS (Infrastructure as a Service) offerings by third party providers. In that context, further automation of the NGS workflows is key to facilitate the routine integration of those services into the clinical practice.

Next Generation Sequencing Workflow Optimization

While next generation sequencing methods have been shown more efficient than traditional Sanger sequencing in the detection of SNPs and INDELs, their specificity (rate of true positive detection for a given genomic variant) and sensitivity (rate of true negative exclusion for a given genomic variant) may still be further improved in clinical practice. The specificity and sensitivity of NGS genomic analysis may be affected by a number of factors:

Biases introduced by the sequencing technology, for instance due to:
  Length of the reads relative to the length of the fragments;
  Too small number of reads (read depth);
  Errors or low quality bases introduced during sequencing;
  Inherent difficulties in counting homopolymer stretches, in particular with pyrosequencing (as in Roche 454 platforms) or semiconductor sequencing (as in Ion Torrent platforms, as described for instance by Rothberg in US patent application 2009/0026082), resulting in insertion and deletion errors;
Biases introduced by the DNA enrichment technology, for instance due to:

Primers or probes non specific binding, for instance due to storing the assay at a low temperature for too long, or due to too small amount of DNA in the sample;

Introduction of sequence errors caused by imperfect PCR amplification and cycling, for instance due to temperature changes;

Suboptimal design of the probes or primers. For example, mutations may fall within the regions of the probes or primers;

Enrichment method limitations. For instance, long deletion may span the amplified region;

Cross-contamination of data sets, read loss and decreased read quality due to fragment tagging with barcodes, adapters and various pre-defined sequence tags;

Chimeric reads in long-insert pair-ended reading.

Biases introduced by the sample itself, for instance due to:

Somatic features, in particular in cancer diagnosis based on tumor sample sequencing;

The type of biological sample, e.g. blood, urine, saliva, and associated sample preparation issues, for instance causing degradation of DNA, contamination with alien DNA, or too low DNA input.

Biases introduced by the genomic data structure of certain regions specifically, for instance due to:

High ratio of GC content in the region of interest;

Presence of homopolymers and/or heteropolymers, that is partial genomic sequence repetitions of one or more nucleotides in certain regions, causing ambiguities in initial alignment, and possibly inherent sequencing errors in particular with the Roche 454 and Ion Torrent sequencer technologies;

Presence of homologous and low-complexity regions;

Presence of non-functional pseudogenes that may be confused with functional genes, in particular in high-repeat genomic regions of the human genome when the DNA fragments are not long enough compared to the read length.

This limits the efficient deployment of NGS in routine genomic analysis applications, as a different genomic data analysis workflow need to be manually organized and configured with different sets of parameters by highly specialized personnel for each application to meet the clinical expectations in terms of specificity and sensitivity. The automation of genomic data processing workflows is particularly challenging as the workflows need to take into account the specific data biases introduced by the upstream NGS biological processes on the one hand and the genomic data structures inherent to the current application on the other hand. In early deployment of genomic testing, a limited number of tests and setups were processed by dedicated platforms, which could be manually setup, configured and maintained by highly skilled specialized staff. This approach is costly and does not scale well as more and more tests have to be conducted in daily operation by a single multi-purpose genomic analysis platform.

Cystic fibrosis genetic diagnosis based on targeted Next Generation Sequencing is an exemplary genomic analysis application which still requires a custom setup, configuration and maintenance by highly specialized bioinformatics experts. The number of repeats in TG dinucleotides (heteropolymers) is typically 11 in the CFTR gene of human chromosome 7, but may vary from 9 to 14 repeats due to insertions and deletions. The latter variants influence the splicing of exon 9 in the CFTR gene and have been associated with the cystic fibrosis disease when the CFTR gene also carries an abbreviated variant of only 5T homopolymers on the polythymidine tract, which is typically of 7 T nucleotide repeats, but may vary from 5 to 9 T nucleotide repeats. Moreover, 12 or 13 TG heteropolymer repeats are also associated with some less common cystic fibrosis pathology, while 11 TG dinucleotides repeats are less associated with the disease (Hefferon et al, "*A variable dinucleotide repeat in the CFTR gene contributes to phenotype diversity by forming RNA secondary structures that alter splicing*", Proc Natl Acad Sci USA 101:3504-3509, 2004 -). The adjacent poly-T and poly-TG tracts polymorphic regions in intron-8 are also under study in other diseases than cystic fibrosis, such as chronic pancreatitis for which an association is suspected with the combination of 5T homopolymers and 12TG heteropolymers (Hegyi et al, "CFTR: A *new horizon in the pathomechanism and treatment of pancreatitis*", Rev Physiol Biochem Pharmacol 2016; 170; 37-66) and congenital bilateral absence of the vas deferens (CBAVD) in male infertility, for which an association with 5T homopolymers and 12TG or 13TG heteropolymers has also been evidenced (Yu et al., "CFTR mutations in men with congenital bilateral absence of the vas deferens (CBAVD): a systematic review and meta-analysis", Human Reproduction, Vol. 27, Issue 1, Jan. 2012, pp 25-35).

As known to those skilled in the art of DNA sequencing, long repeats of mononucleotides and dinucleotides in the DNA sequence induce more experiment errors, in particular due to a decreased accuracy of the PCR amplification. Moreover, DNA sequence alignment errors are common in repetitive regions; for instance in the CFTR context, as pointed out by Trujillano et al in "*Next generation diagnostics of cystic fibrosis and CFTR-related disorders by targeted multiplex high-coverage resequencing of CFTR*" in J Med Genet 2013 50: 455-462 originally published online May 17, 2013 (doi: 10.1136/jmedgenet-2013-101602), the repetitiveness of the sequence at the nucleotide level makes it difficult to determine the TG-T haplotype using standard variant calling algorithms in the context of Next Generation Sequencing, which required the authors to develop an in-house script that scans the very raw sequencing data of each sample for possible combinations of TG repeats (heteropolymers) and T repeats (homopolymers). As will be apparent to those skilled in the art of next generation sequencing genomic analysis, the customization of the bioinformatics analysis tools also depends upon the CFTR assay characteristics and the sequencing technology. For instance Lee et al., "*Replacing CFTR Sanger Sequencing in the Clinical Lab with a Reliable, Targeted Next-Generation Sequencing Assay*" J Genet Genome Res 2014, 1:1 proposes an assay which specifically targets the poly-T and poly-TG tracts, while pointing out that the sensitivity and specificity of the NGS genomic analysis results strongly depends upon the tailor-made customization of the bioinformatics workflow algorithms to adapt to both the target enrichment technology and the sequencing technology specific bias. Lee et al. for instance observed that the primer trimming function in the standard Illumina MiSeq Reporter resulted in unreliable variant calling in regions neighboring primer sequences, as standard variant calling algorithms do not discriminate between a true nucleotide deletion or a sequencing error in the beginning of the read near in the trimmed off primer sequence. Lee et al. therefore proposed to to increase the accuracy and sensitivity of calls near primer binding sites by customizing their bioinformatics pipeline to cross check variants on and near primer regions using both trimmed and untrimmed reads. While suitable for research applications in well-defined laboratory setups with a limited size of the sample sets to analyze for sole scientific, statistical validation purposes, the prior art approaches do not scale well to with the mass-deployment of NGS-based genomic data analysis, as they require a specific assay and/or a custom bioinformatics workflow tailored to a single NGS sequencing equipment.

A bioinformatics method to better detect insertion and deletion in a homopolymer region and detecting the corresponding heterozygosity was for instance described in US patent application 2014/0052381 by Utirametur. Utirametur observed that in an NGS genomic analyzer workflow, the read alignment is not necessarily correct, but it may be possible to determine the heterozygosity from the distribution of base calling residuals based on measured and model-predicted values in the homopolymer regions by using a Bayesian peak detection approach and best-fit model, as homozygous regions tend to have a unimodal distribution while heterozygous regions tend to have a unimodal distribution. From the best-fit model, it is also possible to derive the homopolymer length value for both alleles in the homozygous (unimodal distribution) case, or two different homopolymer length value, one for each allele, in the heterozygous case (bimodal distribution). While this method may facilitate the identification of the length of an independent homopolymer region, it does not apply well to the case where a first homopolymer or heteropolymer region is associated with an upstream second homopolymer or heteropolymer region. Indeed, in this scenario the read alignment errors for both regions interfere and the resulting read coverage signal becomes too noisy to rely upon separate analysis of the length of each region.

There is therefore a need for a better solution to automatize the genomic data processing variant calling workflows for data-driven medical applications, so that the same genomic data processing platform may operate on a diversity of genomic data as may be generated from different next-generation sequencing laboratory setups while optimizing the specificity and the sensitivity of the variant calling results to improve research and clinical practice over the prior art methods in genomic data contexts involving a challenging combination of homopolymer and heteropolymer nucleotide repeats detection.

BRIEF SUMMARY

A method and a genomic data analyzer for identifying, with a processor, a genomic variant scenario as the combination of at least two genomic sequence variants associated with a nucleotide repeat pattern in a patient sampleare described, comprising:

(a) obtaining a plurality of patient data sequence reads from an enriched genomic sample of a patient;

(b) obtaining a plurality of control data sequence reads from an enriched genomic control sample;

(c) measuring a probability distribution of the length of a first repeat pattern, in the plurality of control data sequence reads, as the expected probability distribution of the length of the first repeat pattern in the control sample, the repeat pattern comprising at least two repeats of a basic motif, the basic motif being a sequence of one or more nucleotides;

(d) for each possible genomic variant of the first repeat pattern relative to the control data first repeat pattern, estimating the expected probability distribution of the length of the first repeat pattern for this genomic variant as a function of this genomic variant and of the measured probability distribution of the length of the first repeat pattern in the plurality of control data sequence reads;

(e) measuring a patient probability distribution of the length of the first repeat pattern in the plurality of patient data sequence reads;

(f) comparing the measured patient probability distribution and the expected probability distribution of the length of the first repeat pattern in the control sample;

(g) for each possible genomic variant of the first repeat pattern, comparing the measured patient probability distribution and the expected probability distribution of the length of the first repeat pattern for this genomic variant;

(h) selecting an estimated patient probability distribution of the first repeat pattern length characterizing a first genomic sequence variant of the patient sample as the expected probability distribution which results in the closest comparison with the measured patient probability distribution;

(i) measuring a probability distribution of the length of a second repeat pattern in the plurality of control data sequence reads as the expected probability distribution of the length of the second repeat pattern in the control sample;

(j) for each possible genomic variant of the second repeat pattern relative to the control data second repeat pattern, estimating the expected probability distribution of the length of the second repeat pattern for this genomic variant as a function of this genomic variant and of the measured probability distribution of the length of the second repeat pattern in the plurality of control data sequence reads;

(k) measuring a patient probability distribution of the length of the second repeat pattern in the plurality of patient data sequence reads;

(l) comparing the measured patient probability distribution and the expected probability distribution of the second repeat pattern in the control sample;

(m) for each possible genomic variant of the second repeat pattern, comparing the measured patient probability distribution and the expected probability distribution of the length of the second repeat pattern for this genomic variant;

(n) selecting an estimated patient probability distribution of the second repeat pattern length characterizing a second genomic sequence variant of the patient sample as the expected probability distribution which results in the closest comparison with the measured patient probability distribution;

(o) estimating a first expected joint probability distribution of the length of the first repeat pattern and of the length of the second repeat pattern for at least one first genomic variant scenario in the plurality of control data sequence reads, a genomic variant scenario being characterized by a first repeat pattern genomic variant and a second repeat pattern genomic variant;

(p) estimating a second expected joint probability distribution of the length of the first repeat pattern and of the length of the second repeat pattern for at least one second genomic variant scenario in the plurality of control data sequence reads;

(q) measuring, read by read, the patient joint probability distribution for the length of the first repeat pattern and the length of the second repeat pattern in the plurality of patient data sequence reads;

(r) comparing the measured patient joint probability distribution and the first expected joint probability distribution for the first genomic variant scenario;
(s) comparing the measured patient joint probability distribution and the second expected joint probability distribution for the second genomic variant scenario;
(t) and selecting the genomic variant scenario characterizing the actual genomic variant scenario for the patient as the scenario which results in the closest comparison.

BRIEF DESCRIPTION OF THE DRAWINGS

FIG. 3 illustrates a mismatched genomic sequence alignment as may result from a standard alignment algorithm on next generation sequencing reads.

FIG. 7a) shows the graphical representation of all possible expected probability distributions of the relative length of repeat patterns for various deletion and insertion scenarios as may be derived from the probability distribution of the relative length in control data with no mutation but subject to experiment error biases, and FIG. 7b) shows the graphical representation of a measured probability distribution for patient data, to be matched to the closest expected probability distribution scenario.

FIG. 8a) illustrates a first variant scenario detection as may result from a standard variant calling algorithm on next generation sequencing reads, whereas FIG. 8b) illustrates an alternative second variant scenario detection, as may result from a different variant calling algorithm on the same set of next generation sequencing reads.

FIG. 9a) shows the exemplary joint probability distribution for respectively the relative length of a first repeat pattern and the relative length of a second repeat pattern as may be measured in a next generation sequencing experiment for the first variant scenario of FIG. 8a), whereas FIG. 9b) shows the exemplary joint probability distribution for respectively the relative length of a first repeat pattern and the relative length of a second repeat pattern as may be measured in a next generation sequencing experiment for the second variant scenario of FIG. 8b).

DETAILED DESCRIPTION

Next Generation Sequencing Analysis System

Figure 1:
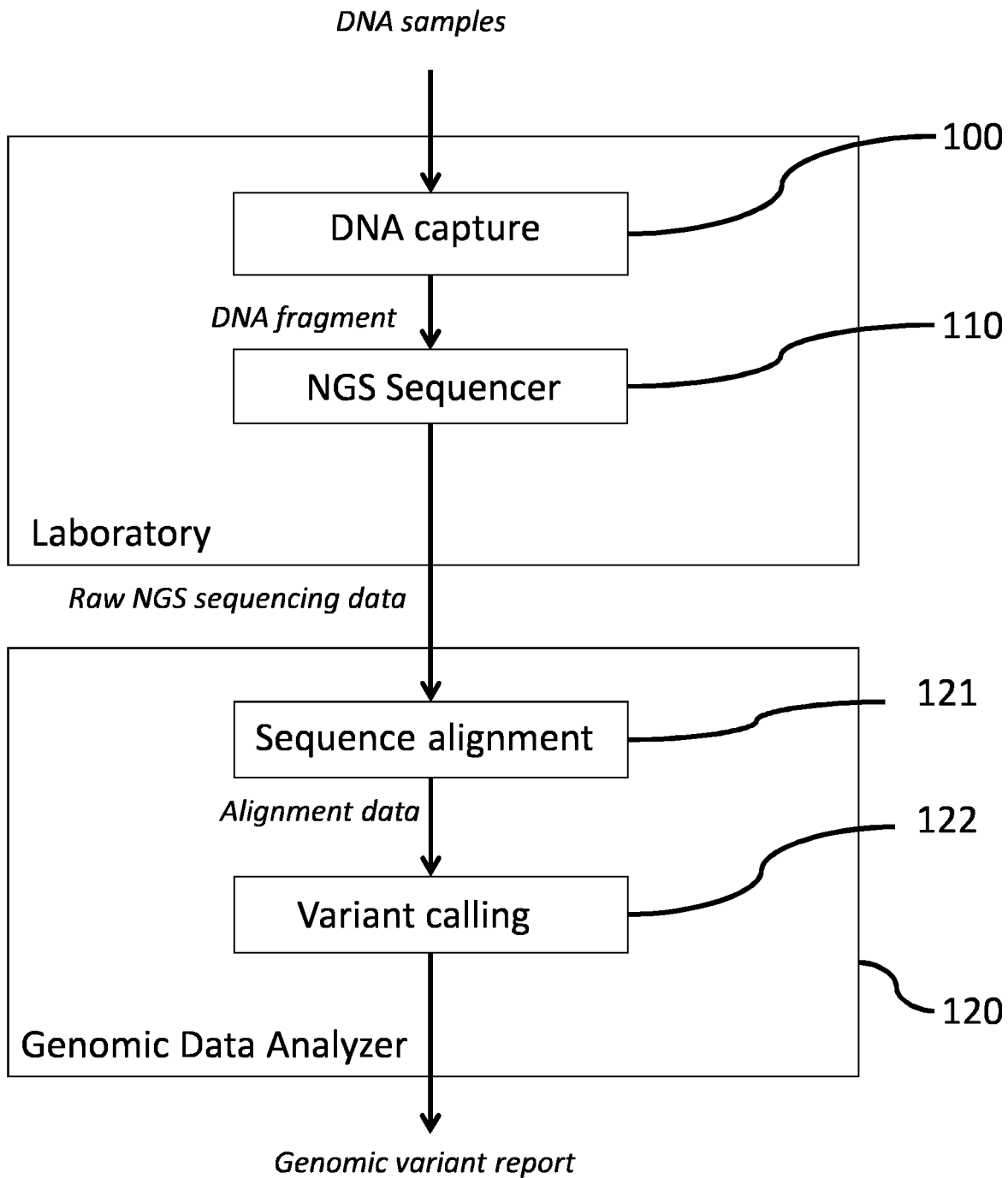
FIG. 1 represents a prior art next generation sequencing system.

FIG. 1 shows an exemplary genomic analysis system comprising a DNA enrichment assay 100, a next generation sequencer 110 and a genomic data analyzer 120.

In a NGS laboratory, a pool of DNA samples is processed by the DNA enrichment assay 100 to generate a library of pooled amplicons (for amplicon-based enrichment) or fragments (for probe-based enrichment) as DNA fragments input to the next generation sequencer 110, each set of amplicons/fragments corresponding to a different sample. The number of amplicons/fragments is application dependent. In some genomic analysis experiments, target enrichment may require 150 primers to enrich 75 different regions to be targeted out of the sample genome, resulting in a set of 75 amplicons for each sample. The number of samples may also be adapted to the next-generation sequencing sequencer 110 parallel processing capability, for instance 48 samples in the form of a library of pooled amplicons may be sequenced in parallel by an Illumina MiSeq sequencer. Other NGS sequencer technologies may be used, such as for instance the Roche 454™ GS Junior or GS FLX, Illumina MiSeq®, or Life Technologies Ion PGM™ sequencers.

The next-generation sequencer 110 analyses the input samples and generates sequence reads in a computer-readable file format representing raw NGS sequencing data. Depending on the NGS technology, one or more files may be output by the NGS sequencer 110. In some embodiments, for instance with Illumina sequencers, the FASTQ file format may be used with two different files for forward and reverse reads or as a single joined file. This text file typically starts with a sequence header marked by a '@' start character, followed by one line of sequence information represented as a string of 'A', 'T', 'C', 'G' nucleotide characters, then by a quality header marked by a '+' start character, followed by one line of quality metrics, one quality score matching each nucleotide read. The format for the quality metrics for each nucleotide in the sequence information string may depend on the sequencer. Some legacy sequencers output the raw sequencing data in the SFF (Standard Flowgram Format) binary file format, which comprises an informative header and the read data. Other embodiments are also possible, for instance some legacy Roche sequencers output multiple FASTQ files for a single patient analysis, while other sequencers, for instance the Ion Torrent PGM sequencers, have migrated to the compressed unmapped BAM file format, as may be recognized from the .basecaller.bam file extension. As known to those skilled in the art of communication systems, the laboratory operates a computing infrastructure to store the resulting raw NGS sequencing data file in a laboratory biobank. The laboratory computing infrastructure connects, with authentication credentials, through a communication network, to the genomic data analyzer 120 and transmits a genomic analysis request comprising the raw NGS sequencing file to the genomic data analyzer 120.

The genomic data analyzer 120 computer system (also "system" herein) 120 is programmed or otherwise configured to implement different genomic data analysis methods, such as receiving and/or combining sequencing data and/or annotating sequencing data.

The genomic data analyzer 120 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. Examples of genomic data analyzer computing systems, environments, and/or configurations include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and the like. In some embodiments, the computer system may comprise one or more computer servers, which are operational with numerous other general purpose or special purpose computing systems and may enable distributed computing, such as cloud computing, for instance in a genomic data farm. In some embodiments, the genomic data analyzer 120 may be integrated into a massively parallel system. In some embodiments, the genomic data analyzer 120 may be directly integrated into a next generation sequencing system.

The genomic data analyzer 120 computer system may be adapted in the general context of computer system-executable instructions, such as program modules, being executed by a computer system. Generally, program modules may include routines, programs, objects, components, logic, data structures, and so on that perform particular tasks or implement particular abstract data types. As is well known to those skilled in the art of computer programming, program modules may use native operating system and/or file system functions, standalone applications; browser or application plugins, applets, etc.; commercial or open source libraries and/or library tools as may be programmed in Python, Biopython, C/C++, or other programming languages; custom scripts, such as Perl or Bioperl scripts.

Instructions may be executed in distributed cloud computing environments where tasks are performed by remote processing devices that are linked through a communications network. In a distributed cloud-computing environment, program modules may be located in both local and remote computer system storage media including memory storage devices.

As illustrated on FIG. 1, the genomic data analyzer 120 may comprise a sequence alignment module 121, which compares the raw NGS sequencing data to a reference genome. The sequence alignment module 121 may be configured to execute different alignment algorithms. Standard raw data alignment algorithms such as Bowtie2 or BWA that have been optimized for fast processing of numerous genomic data sequencing reads may be used, but other embodiments are also possible. The alignment results may be represented as one or several files in BAM or SAM format, as known to those skilled in the bioinformatics art, but other formats may also be used, for instance compressed formats or formats optimized for order-preserving encryption, depending on the genomic data analyzer 120 requirements for storage optimization and/or genomic data privacy enforcement.

The resulting alignment data may be further filtered and analyzed by a variant calling module 122 to retrieve variant information such as SNP and INDEL polymorphisms. The variant calling module 122 may be configured to execute different variant calling algorithms. The resulting detected variant information may then be output by the genomic data analyzer module 120 as a genomic variant report for further processing by the end user, for instance with a visualization tool, and/or by a further variant annotation processing module (not represented).

The genomic data analyzer 120 may be adapted to automatically detect, with a processor, a set of characteristics that uniquely determine the input sequencing data and corresponding genetic context, the DNA enrichment context such as the sample type or laboratory process characteristics, the DNA enrichment technology such as the targeted enrichment target kit or capture probe assay characteristics, and/or the NGS sequencing technology. As will be apparent to those skilled in the art of next generation sequencing, these experimental characteristics may cause specific biases in the sequence alignment and/or the variant calling results.

The proposed genomic data analyzer system 120 may thus serve next generation sequencing genomic analysis requests from different labs that are independently operating different sequencer technologies and different DNA enrichment technologies on different samples for different genes. The proposed genomic data analyzer system 120 may automatically detect a set of characteristics from the input data and requests received from the laboratory and may adapt the configuration of the sequence alignment module 121 and the variant calling module 122 accordingly, without requiring a time consuming and costly manual setup to minimize the data biases possibly induced by each different biological workflow. As will be apparent to those skilled in the art, there may be dozens or even hundreds of different clinical laboratory setups for multiple sourcing laboratories operating with the same genomic analyzer 120, and this number and diversity is likely to further increase with the deployment of additional technologies and assays as the NGS-based personalized medicine clinical practice develops.

Depending on the detected genomic experiment characteristics, the genomic data analyzer 120 may configure the sequence alignment module 121 to operate additional data processing steps and/or use different sets of configuration parameters such that the data biases caused by the genomic experiment characteristics are minimized.

Depending on the detected input characteristics, the genomic data analyzer may further configure the variant calling module 122 to operate additional data processing steps and/or use different sets of configuration parameters such that the data biases caused by the genomic experiment characteristics are minimized.

Depending on the results of the initial sequence alignment by the sequence alignment module 121, the genomic data analyzer 120 may be further adapted to identify next generation sequencing data alignment biases that become apparent when analyzing the alignment data. The genomic data analyzer may accordingly configure the sequence alignment module 121 to execute an additional step of re-alignment of the raw NGS sequencing data. This re-alignment may be constrained by additional parameters as may be determined from the initial alignment results. In a possible embodiment the re-alignment is applied specifically on a sub-region of the genomic sequence. The resulting re-alignment data may be further filtered and analyzed by the variant calling module 122 to output a more relevant genomic variant report with increased sensitivity and specificity for variant detection.

Depending on the results of the variant calling by the variant calling module 122, the genomic data analyzer 120 may be further adapted to identify variant calling biases that become apparent when calling variants on the alignment data. The genomic data analyzer may accordingly configure the variant calling module 122 to execute an additional step of re-calling variants on all or part of the alignment data. This refined variant calling step may be constrained by additional parameters as may be determined from the former alignment and/or re-alignment and/or variant calling results. In a possible embodiment variants are specifically called on a subset of the aligned genomic data. The resulting refined variant calling data may be further combined with the standard variant calling results by the variant calling module 122 to output a more relevant genomic variant report with increased sensitivity and specificity for variant detection. In a possible embodiment, some variant calling results may be excluded from the genomic variant report as identified possibly biased by the variant calling module 122, so that a more relevant genomic variant report is generated by the genomic data analyzer 120 with increased sensitivity and specificity for variant detection.

Figure 2:
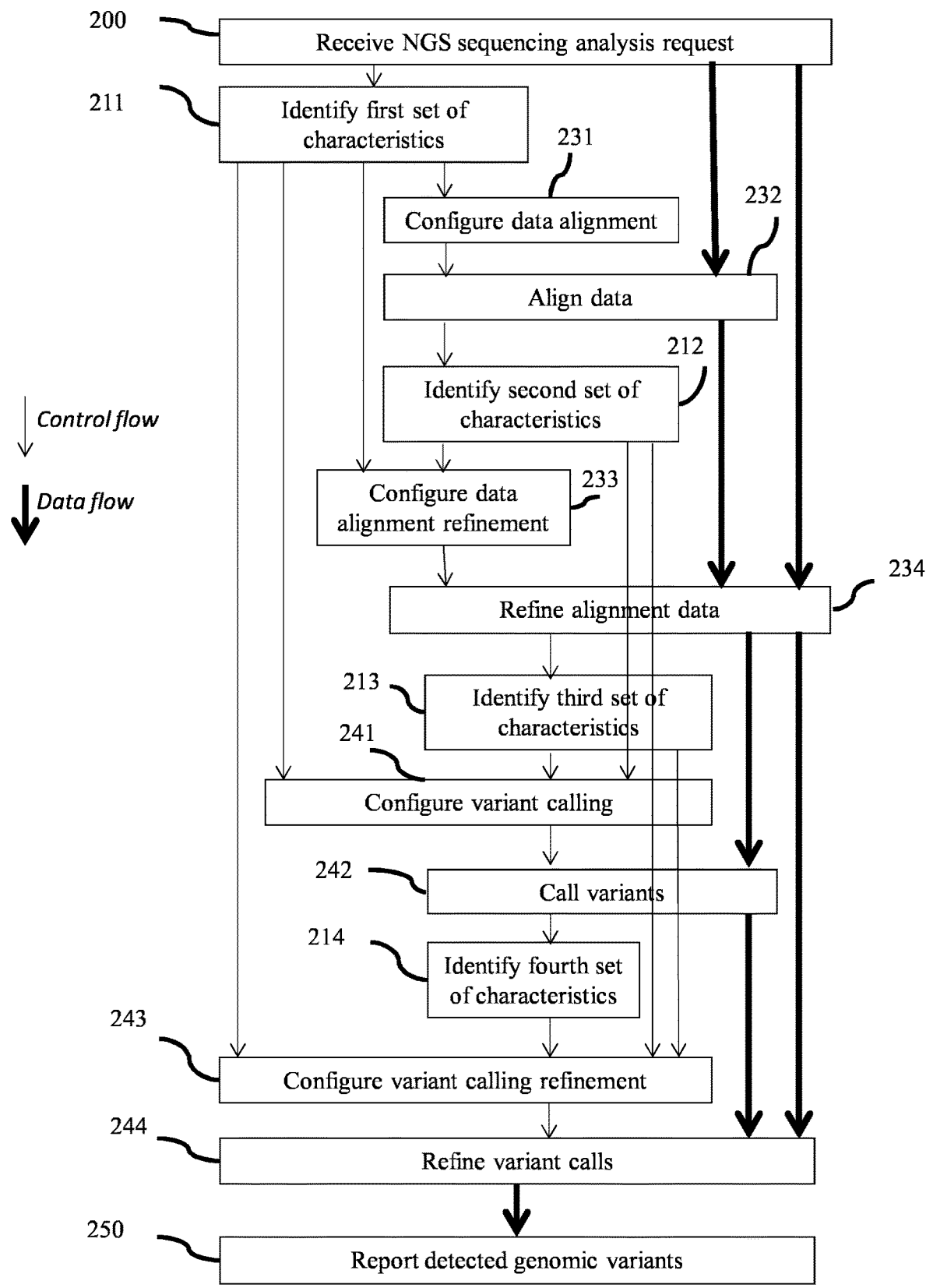
FIG. 2 shows the flowchart of a next generation sequencing genomic analysis workflow.

FIG. 2 shows accordingly a possible genomic analysis workflow for the genomic data analyzer 120, comprising:

receiving 200 a next generation sequencing analysis request;

identifying 211 a first set of characteristics associated with the next generation sequencing analysis request, the first set of characteristics comprising at least a target enrichment technology identifier, a sequencing technology identifier, and a genomic context identifier;

configuring 231 a data alignment module 121 to align the input sequencing data in accordance with at least one characteristic of the first set of characteristics;

aligning 232, with the configured data alignment module 121, the input sequencing data to a genomic sequence, and reporting the alignment data into a raw alignment data file;

identifying 212 a second set of characteristics associated with the alignment data from the raw alignment data file, the second set of characteristics comprising at least a data alignment pattern identifier;

configuring 233 the data alignment module 121 to refine at least one subset of the input sequencing data in accordance with at least one characteristic of the first set of characteristics and at least one characteristic of the second set of characteristics;

refining 234, with the configured data alignment module 121, the subset of the input sequencing data to produce a refined alignment data file;

identifying 213 a third set of characteristics associated with the re-alignment data from the refined alignment data file, the third set of characteristics comprising at least a genomic context identifier;

configuring 241 a variant calling module 122 to detect variants associated with the refined alignment data in accordance with at least one characteristic of the first set of characteristics, at least one characteristic of the second set of characteristics, and at least one characteristic of the third set of characteristics;

detecting 242 a first set of genomic variants, with the configured variant calling module 122, in the refined alignment data;

identifying 214 a fourth set of characteristics associated with the detected genomic variants, the fourth set of characteristics comprising at least a variant calling refinement identifier;

configuring 243 the variant calling module 122 to detect variants associated with the refined alignment data in accordance with at least one characteristic of the first set of characteristics, at least one characteristic of the second set of characteristics, at least one characteristic of the third set of characteristics and at least one characteristic of the fourth set of characteristics;

detecting 244 refined genomic variants, with the configured variant calling module 122, in the refined alignment data and the detected genomic variants, to produce a refined set of genomic variants;

reporting 250 the refined set of genomic variants.

The generic, multi-purpose genomic data analyzer 120 thus facilitates the analysis and reporting of multiple different genomic variants from raw next generation sequencing data received from a diversity of clinical setups operated by multiple sourcing laboratories without requiring dedicated manual configuration or exhaustive metadata documentation to adapt to each combination of biological setup and diagnosis context for each clinical analysis.

Refined Variant Calling Method—Exemplary Embodiment

An exemplary embodiment of the proposed refined variant calling 244 method will now be described in more detail with the example of a cystic fibrosis genetic diagnosis application. The fully automated genomic data analysis workflow of FIG. 2 operates on genomic data sourced from at least one next generation sequencing laboratory. As an example, the laboratory may operate an Illumina sequencer MiSeq® with Reagent Kit v3, which has a sequencing capacity of 15Gb@2×300 bp for up to 25 millions total reads, and the Multiplicom CFTR MASTR™ Dx targeting the CFTR gene associated with mutations frequently causing cystic fibrosis in individuals from European descent. This assay is dedicated to the detection, with a multiplex amplification technology, of the CFTR gene mutations P causing cystic fibrosis. The latter technology uses 48 amplicons of 300 bp to 450 bp and primer probes of 20 bp to 30 bp, and is typically operated with pair-ended read length of 250 bp pair-ended reads.

The genomic data analyzer 120 receives 200 an NGS sequencing analysis request from the laboratory, comprising two raw sequencing files from the Illumina sequencer, each file corresponding to a different reading direction (3' to 5' and 5' to 3' respectively) of the pair-ended reads. The genomic data analyzer 120 identifies 211 a first set of characteristics of the genomic analysis experiment by searching for headers, sequence patterns, adapter patterns and/or gene context patterns in the raw sequencing input files that match one of the laboratory information listings. In this analysis workflow, the genomic data analyzer 120 identifies 211 the sequencer technology identifier as Illumina MiSeq® Reagent Kit V3 from the laboratory information, confirmed by the pair of two FASTQ files, which comprise the Illumina headers and Illumina specific adapter patterns.

The genomic data analyzer 120 also identifies 211 from the first set of characteristics and/or the presence of assay-specific primer and/or sequencing adaptor patterns in the input FASTQ files that the target enrichment technology is the Multiplicom CFTR MASTR™ Dx assay and the genomic context identifier as the CFTR gene covered by this specific amplicon-based kit.

As a function of at least one of these first characteristics, the genomic data analyzer 120 configures 231 the data alignment module 121 to execute 232 a first raw data alignment. The data alignment module 121 may also execute 232 pre-processing steps such as removing the Multiplicom specific adapters from the reads and/or merging the pair-ended files into a single merged file.

The data alignment module 121 aligns 232 to a reference genomic sequence, with a raw data alignment algorithm as known to those skilled in the art of bioinformatics, the pre-processed raw sequencing data to produce a data alignment file. Standard algorithms such as Bowtie2 or BWA that have been optimized for fast processing of numerous genomic data sequencing reads may be used, but other embodiments are also possible. The resulting data alignment file may be represented as one or several files in BAM or SAM format, but other embodiments are also possible, in particular the data alignment module 121 may also execute 232 post-processing steps such as compressing and/or encrypting the alignment data, for instance with an order-preserving encryption scheme, depending on the genomic data analyzer 120 requirements for storage optimization and/or genomic data privacy enforcement along the genomic analysis workflow processing.

The genomic data analyzer 120 may then automatically derive 212 a second set of characteristics from the results of data alignment 232, such as a specific data alignment pattern requiring refinement of the alignment and/or the variant calling algorithms. The genomic data analyzer may for instance detect the presence of alignment mismatches especially at the beginning and/or the end of the reads ("soft clipping"), as may be due to primer mispriming. This frequent bias in amplicon-based technologies may indeed cause either:

False positives, when a mispriming artifact is present in enough reads to be misaligned to the reference genome, which will cause a wrong variant calling 242 interpretation as a SNP in the DNA sample;

False negatives, when the alignment module 121 cannot discriminate between mispriming artifacts in certain reads and the correct amplicon data in other reads, causing the corresponding regions to be soft clipped by the data alignment module 121, which will in turn cause the variant calling 242 to miss possible variants of pathological relevance in the correct amplicon data.

Soft clip patterns correspond to sequencing data at the 5' or 3' boundaries of the reads that could not be properly aligned by the data alignment module 121 raw alignment algorithms 232. Soft clipped alignments are specifically marked in the CIGAR string of the alignment data file, so the corresponding patterns can be easily identified after data alignment 232. As known to those skilled in the art of Next Generation Sequencing, soft clipping information may then be re-mapped in the genomic analysis workflow with specific algorithms in order to further detect structural variants of potential clinical relevance.

The genomic data analyzer 120 may thus automatically identify 212 the reads with soft clipping regions, from the results of the data alignment 232, and configure 233 the data alignment module 121 to operate a further data re-alignment 234 on those reads specifically by taking into account the primer anchors information corresponding to the specific DNA enrichment technology, here the Multiplicom CFTR MASTR™ Dx list of primer sequences, in the alignment algorithm. As will be apparent to those skilled in the art of bioinformatics, a more robust algorithm than Bowtie2 or BWA may be used specifically on those regions, even if less computationally efficient. Indeed, only a subset of the whole NGS data needs to be re-aligned this way and the proposed workflow is fully automated, so the overall computational efficiency performance of the genomic data analyzer 120 is not be significantly impacted, while this data re-alignment refinement automation enables to increase the specificity and sensitivity of the genomic data analyzer 120 to be comparable to that obtained with manual trial-and-errors setups of the prior art research practice. Examples of such algorithms have been described for instance by Suzuki et al. in "*ClipCrop: a tool for detecting structural variations with single-base resolution using soft-clipping information*", BMC Bioinformatics 2011 12(*Suppl* 14):S7 and by Schröder et al in "*Socrates: identification of genomic rearrangements in tumour genomes by re-aligning soft clipped reads*", Bioinformatics (2014), but other embodiments are also possible. In particular the most efficient re-alignment algorithm may be automatically configured 233 by the proposed genomic data analyzer 120 as a function of both the genomic context and the raw alignment data soft clip patterns.

Figure 4:
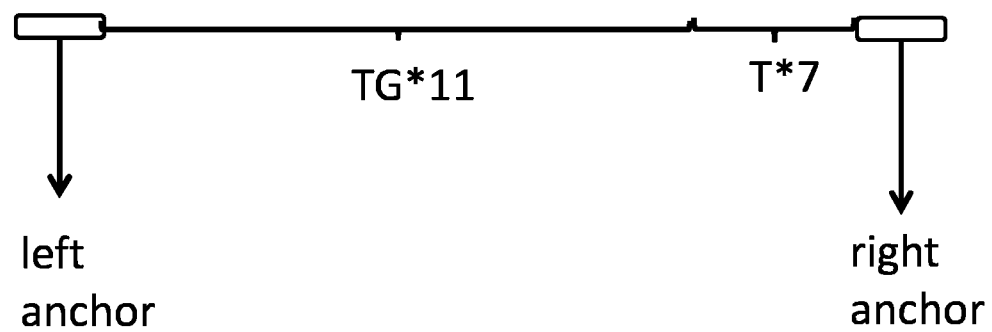
FIG. 4 shows possible left and right anchor patterns around the poly-T/TG repetitive area in the CFTR gene DNA sequence.

Depending on the genomic context identifier, the genomic data analyzer 120 may also identify from the alignment data the presence of some regions that are particularly challenging to align, such as homopolymer regions, heteropolymer regions, or other regions with specific repeat patterns. For instance, as known to those skilled in the art of genomics, some of the human gene CFTR mutations causing pathologies such as cystic fibrosis and CBAVD are characterized by a shorter repeat of the T nucleotide basic motif (poly-T tract) in conjunction with a longer string of repeats of the TG dinucleotide basic motif (poly-TG tract). In other genes than CFTR, genomic mutations may be characterized by other combinations of repeats of basic motifs, for instance a string of repeats of the TGA trinucleotide basif motif (poly-TGA tract) in combination with the shorter repeat of the T nucleotide basic motif (poly-T tract). As will be apparent to those skilled in the art of genomics, other repetitive DNA sequence motifs may be encountered in various genomic analysis applications. Proper alignment of corresponding next generation sequencing reads is particularly challenging as those multiple repeats cause alignment ambiguities. FIG. 3 shows an example of reads that cannot be independently aligned to the reference sequence Ref by a standard algorithm which aligns the reads independently from each other, as the Bowtie2 or BWA algorithms do, in such a genomic context. The genomic data analyzer 120 may thus automatically identify 212 from the results of the raw data alignment 232 a specific genomic context requiring refinement on the reads overlapping those ambiguous regions. The genomic data analyzer 120 may accordingly configure 233 the data alignment module 121 to operate a further data re-alignment 234 on those reads to identify other possible alignment solutions, such as for instance by taking into account the PCR error rate and comparing reads to each other. In a possible embodiment, based on the genomic context identifier, the data re-alignment 234 may comprise searching the raw read sequences for a left anchor known from the reference genome as a non-repetitive nucleotide pattern to be found left to the repetitive region, for instance the TGA pattern in FIG. 4, and a right anchor known from the reference genome as a non-repetitive nucleotide pattern to be found right to the repetitive region as a non-repetitive nucleotide pattern, for instance the AAC pattern in FIG. 4.

The genomic data analyzer 120 may then use the target enrichment technology identifier to configure 241 the variant calling module 122 to execute different variant calling algorithms in accordance with the initially identified genomic context identifier (e.g. CTFR) and the specific genomic context refinement identified from the raw alignment results (e.g. the presence of certain Poly-T and Poly-TG repeat patterns in the data). The variant calling module 122 calls 242 variants on the refined alignment data to produce a first VCF file. In some cases, the resulting variants may not be accurate enough to be reported by the genomic data analyzer 120. The genomic data analyzer 120 may thus identify 214 a fourth set of characteristics such as the need for variant phasing (that is, associating variants with the chromosome alleles on which they occur) from the initial variant calling results, and configure 243 the variant calling module 122 to refine 244 the variant calling data, depending on characteristics such as whether the adjacent variants are presented in the same reads.

A possible embodiment of a refined variant calling method 244 suitable to better sort out ambiguous variants combining multiple interdependent homopolymer tracts and/or heteropolymer tracts will now be described in more detail, in the exemplary application of the CFTR mutations genetic diagnosis. As known to those skilled in the art of bioinformatics, the genomic data analyzer 120 may receive from the laboratory raw NGS sequencing data corresponding to patients as well as control data, the patients and the control data being generated with the same experimental process (DNA capture 100 and NG sequencer 110). Due to the lower DNA sequencing experiment accuracy in the presence of homopolymer and heteropolymer nucleotide repeats, false insertions and deletions may be detected even when there was actually no mutation in the samples. In state of the art laboratory practice, up to 30% of the TG heteropolymers may be missing thus analyzed as deletions due to PCR amplification errors in those regions, which introduces a significant statistical bias and thus decreases the accuracy of the genomic analysis. The first variant calling challenge therefore consists in properly estimating the length of the repetitive sequence patterns, such as the TG heteropolymer tract and/or the T homopolymer tract in the CFTR gene. Indeed, the measured length follows a discrete probability distribution of the length of the repeat patterns ("distribution-length") that may depend both on the experiment bias and the actual genomic variant. For increased sensitivity and specificity in the genomic analysis workflow, it is desirable to decrease the contribution of the experiment bias in the measurement data as much as possible.

In a possible embodiment the distribution of the length may be measured as the discrete probability distribution of the absolute length of a repeated nucleotide pattern in a set of genomic sequence data reads with sufficient coverage. In another possible embodiment the distribution length may be measured as the discrete normalized probability distribution of the relative length of a repeated nucleotide pattern in a set of genomic sequence data reads with sufficient coverage, relative to the wild type repeated pattern most commonly found without mutation. The repeated nucleotide pattern may be a homopolymer, as the repetition of a single nucleotide, or a heteropolymer, as the repetition of two or more nucleotides. In the CFTR genomic analysis application, the homopolymer may be the poly-T pattern, the absolute length for this pattern may usually be measured in the range of 5 to 9, or the relative length in the range of −2 (2 deletions) to 2 (2 insertions) with 0 representing the wild type repeat pattern of 7 T nucleotides without mutation. In the CFTR genomic analysis application, the heteropolymer may be the poly-TG pattern, the absolute length for this pattern may usually be measured in the range of 9 to 14, or the relative length in the range of −2 (2 deletions) to 3 (3 insertions) with 0 representing the wild type repeat pattern of 11 TG dinucleotides without mutation.

In a possible embodiment, the refined variant calling method 244 may thus comprise:
  (a) obtaining a plurality of patient data sequence reads from an enriched genomic sample of a patient;
  (b) obtaining a plurality of control data sequence reads from an enriched genomic control sample;
  (c) measuring a probability distribution of the length of a first repeat pattern, in the plurality of control data sequence reads, as the expected probability distribution length of the first repeat pattern of the control sample, the repeat pattern comprising at least two repeats of a basic motif, the basic motif being a sequence of one or more nucleotides;
  (d) for each possible genomic variant of the first repeat pattern relative to the control data first repeat pattern, estimating the expected probability distribution of the length of the first repeat pattern for this genomic variant as a function of this genomic variant and of the measured probability distribution of the length of the first repeat pattern in the plurality of control data sequence reads;
  (e) measuring a probability distribution of the length of the first repeat pattern in the plurality of patient data sequence reads;
  (f) comparing the measured patient probability distribution and the expected probability distribution of the first repeat pattern of the control sample;
  (g) for each possible genomic variant of the first repeat pattern, comparing the measured patient probability distribution and the expected probability distribution of the length of the first repeat pattern for this genomic variant;
  (h) selecting an estimated patient probability distribution of the first repeat pattern length characterizing a first genomic sequence variant of the patient sample as the expected probability distribution which results in the closest comparison with the measured patient probability distribution.

In a possible further embodiment, the refined variant calling method 244 may further comprise:
  (i) measuring a probability distribution of the length of a second repeat pattern in the plurality of control data sequence reads as the expected probability distribution length of the second repeat pattern of the control sample;
  (j) for each possible genomic variant of the second repeat pattern relative to the control data second repeat pattern, estimating the expected probability distribution of the length of the second repeat pattern for this genomic variant as a function of this genomic variant and of the measured probability distribution of the length of the second repeat pattern in the plurality of control data sequence reads;
  (k) measuring a probability distribution of the length of the second repeat pattern in the plurality of patient data sequence reads;
  (l) comparing the measured patient probability distribution and the expected probability distribution of the second repeat pattern of the control sample;
  (m) for each possible genomic variant of the second repeat pattern, comparing the measured patient probability distribution and the expected probability distribution of the length of the second repeat pattern for this genomic variant;
  (n) selecting an estimated patient probability distribution of the second repeat pattern length characterizing a second genomic sequence variant of the patient sample as the expected probability distribution which results in the closest comparison with the measured patient probability distribution.

In the exemplary application of CFTR genomic analysis, the refined variant calling method 244 may apply the above described process for the TG heteropolymer tract, as a first repeat pattern, as well as for the T homopolymer tract, as a second repeat pattern. It is then possible to better estimate the length of the TG and the T nucleotide repeats while minimizing the biases caused by the experiment errors, thanks to taking into account the control data distribution-lengths in estimating the expected distribution-lengths for various insertion and deletion scenarios on each possible repetitive sequence pattern. As will be apparent to those skilled in the art of bioinformatics, this method will significantly improve the accuracy of the repetitive pattern length estimation provided that the next generation sequencing reads have a large enough statistical coverage.

Figure 5:
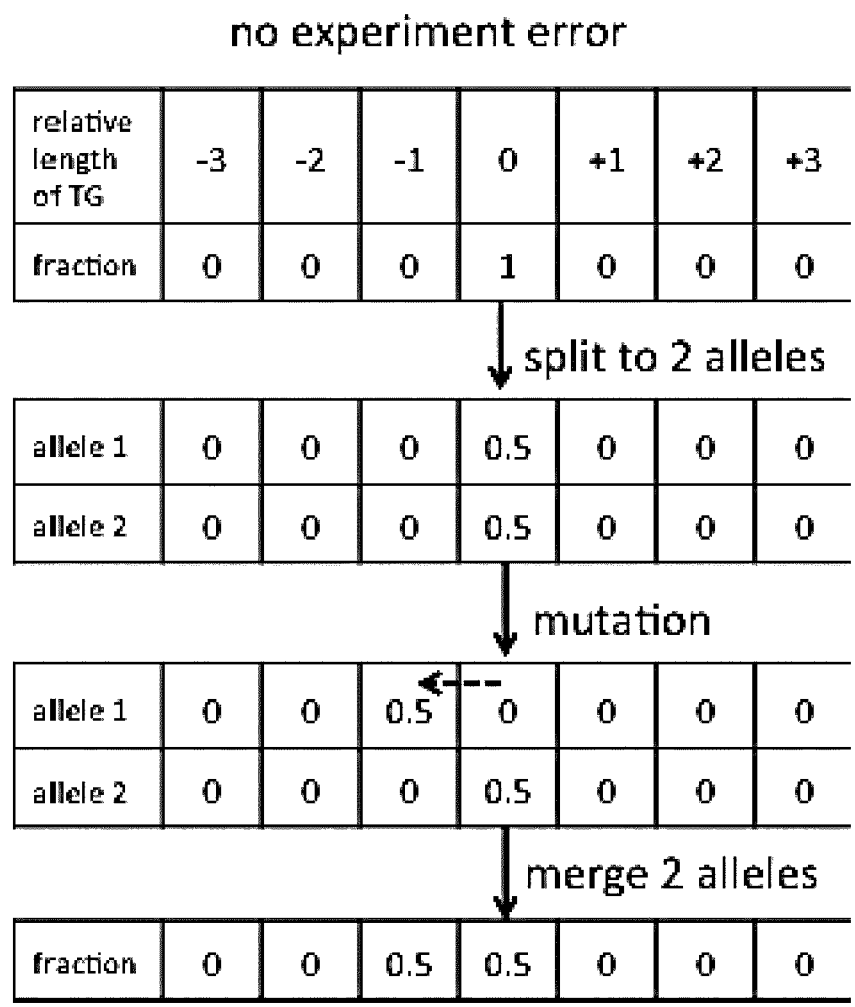
FIG. 5 shows an exemplary probability distribution of the expected relative length of a repeat pattern for a control data with no experiment error and no mutation, and the resulting expected shifted probability distribution for a heterozygous single deletion mutation in the repeat pattern.

The distribution of expected samples relative to the standard 11 TG repeats tract as obtained by this method is illustrated by FIG. 5 for a control data with no mutation and no experiment error bias, and a scenario of a single basic motif deletion, for instance the deletion of a TG basic motif in a single allele in the CFTR gene poly-TG heteropolymer tract (heterozygous TG deletion—10-TG pattern on one allele, and 11-TG pattern on the other allele). This corresponds to the ideal, theoretical case where each allele contributes 50% of the distribution-length measurement, thus respectively a length of 10 TG repeats and a length of 11 TG repeats are expected to be measured from the re-alignment data, each with an equal probability of 0.5 in the normalized discrete probability distribution the length of the TG tract.

Figure 6:
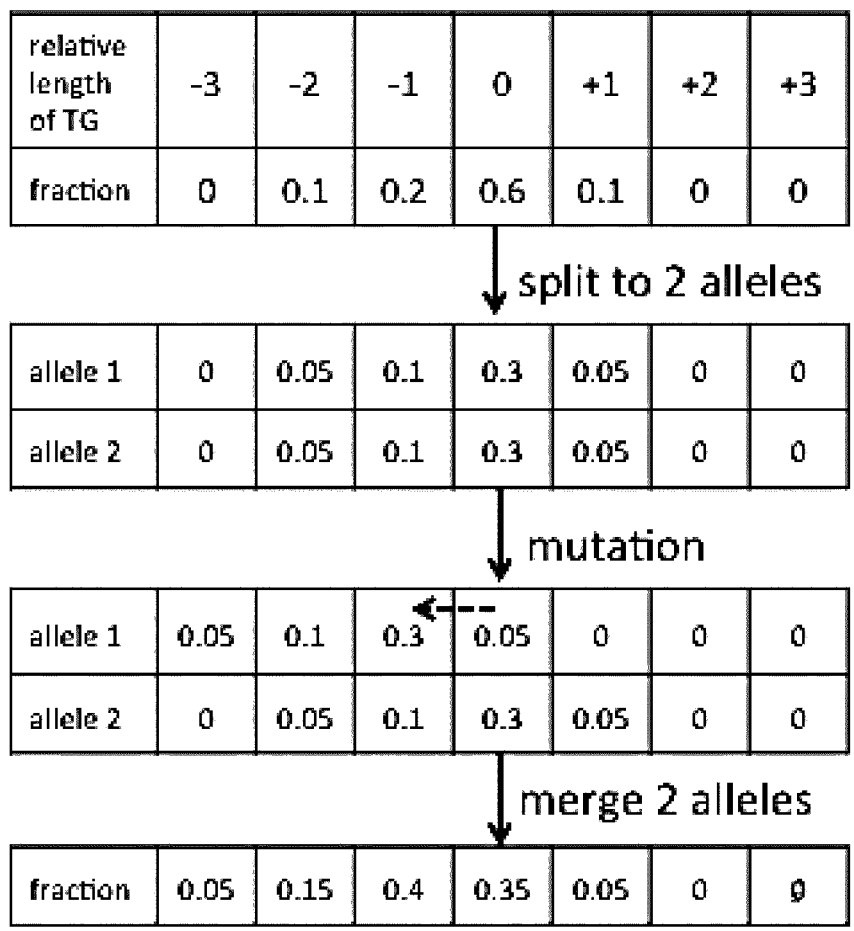
FIG. 6 shows an exemplary probability distribution of the measured relative length of a repeat pattern for a control data with no mutation but subject to an experiment bias, and the resulting expected shifted distribution for the measured relative length of the repeat pattern for patient data with a heterozygous single deletion mutation.

Another exemplary distribution of expected samples relative to the standard 11 TG repeats tract is illustrated by FIG. 6 for a more realistic control data with no mutation but subject to an experiment error bias, which causes erroneous shorter lengths measurements of 2 deletions (10% of the control coverage data) or 1 deletion (20% of the control coverage data) and erroneous longer lengths measurements of 1 insertion (10% of the control coverage data), so that only 60% of the coverage data corresponds to the actual length of the repetitive region, for instance an actual length of 11 TG dicleotides for the standard homozygous 11-TG pattern with no mutation on the CFTR gene for the control data. The measured discrete probability distribution of the pattern length for the control data will be biased accordingly, and this experiment-induced bias may thus be taken into account in estimating the expected discrete probability distribution of the pattern length for each possible mutation variant scenario for improved sensitivity and specificity. As an example, FIG. 6 shows the resulting expected discrete probability distribution of the pattern length estimation for the scenario of a single basic motif deletion, for instance the deletion of a TG basic motif in a single allele in the CFTR gene poly-TG heteropolymer tract (heterozygous TG deletion—10-TG pattern on one allele, and 11-TG pattern on the other allele). On the mutated allele 1 the whole probability distribution of the pattern length may be shifted towards the left, due to the actual deletion of a TG basic motif. As both alleles equally contribute to the overall measurement data, their contributions may be simply summed up and averaged to provide the expected probability distribution of the pattern length for this single deletion mutation scenario, while taking into account the experiment error bias from the control data: in this example illustration, we can expect that 5% of a single-deletion mutation patient data will be measured as carrying 3 deletions, 15% as carrying 2 deletions, 40% as carrying 1 deletion (correct result), 35% as carrying no mutation, and 5% as carrying a single insertion of the basic motif, for instance the TG dinucleotide in the poly-TG heteropolymer tract on the CFTR gene.

FIG. 7a) shows exemplary expected discrete probability distributions of the repeat region lengths relative to the genome reference length for a diversity of scenarios ranging from a homozygous double deletion (top left—length of −2 compared to the reference centered on 0) to a homozygous double insertion (bottom right—length of +2 compared to the reference centered on 0) when the experiment bias causes the following erroneous probability distribution measurement in the control data with no mutation (0/0 scenario): 40% measurement of no mutation, 30% measurement of a single deletion (length of −1 compared to the reference centered on 0), 30% measurement of a single insertion (length of +1 compared to the reference centered on 0).

As will be apparent to those skilled in the art of statistics, the variant calling module 122 may apply different mathematical methods, for instance a statistical distance measure, to compare the measured normalized discrete probability distribution of the length in the patient data, as illustrated for instance by FIG. 7b), with the expected normalized discrete probability distribution of the length for each scenario, as illustrated for instance by FIG. 7a). The variant calling module 122 may then select the closest comparison scenario as the scenario which results in the minimal estimated distance.

Various methods may used to this end, such as for instance the minimization of the mean square error between the measured and the expected statistical distributions. As will be apparent to those skilled in the art, either the relative lengths (relative to the most common wild type) or the absolute lengths may be used in the discrete probability model, one being a simple shift of the reference coordinates compared to the other. In a possible embodiment the statistical distance between the measured absolute discrete probability distribution of the length in the patient data and the expected absolute discrete probability distribution of the length for a variant scenario of i repeats of a nucleotide pattern in the first allele and j repeats in the second allele may be computed as the Euclidean distance:

$$d_{i|j} = \sqrt{\sum_{l=0}^{L}(P_{i|j,l} - P_l)^2}$$

where L is the maximum repeat length, i|j corresponds to the variant of i repeats on the first allele and j repeats on the second allele, $P_l$ is the probability of observing a repeat with exact length l from the patient data, $P_{i|j,l}$ is the probability of observing a repeat with exact length l from the reference (control) data, with the distribution shifted by i repeats in the first allele and j repeats in the second allele; and $d_{i|j}$ is the distance between the shifted distribution and the observed distribution, which may then be calculated for all possible combinations of i|j. The pattern with the minimum $d_{i|j}$ is given as the prediction.

In FIG. 7, the [0/1] variant scenario will be selected accordingly (heterozygous single insertion, for instance 11-TG on one allele and 12-TG on the other allele in the CFTR example).

The above proposed methods enable to reliably estimate the unbiased respective probability distributions of the lengths of the first repeat pattern (for instance, the repeat of the TG heteropolymer basic motif) and the second repeat pattern (for instance, the repeat of the T heomopolymer basic motif) in the patient sample data. However, there are still possible ambiguities in searching for the actual variants. As an illustration, in the particular exemplary application of CFTR poly-T/TG genomic variant detection and characterization, if both the TG heteropolymer and the T homopolymer patterns are heterozygous, there are still two possibilities of phasing actual variants.

The method and genomic data analyzer for detecting and characterizing genomic sequence variants may thus further comprise:
(o) estimating a first expected joint probability distribution of the length of the first repeat pattern and of the length of the second repeat pattern for at least one first genomic variant scenario in the plurality of control data sequence reads, a genomic variant scenario being characterized by a first repeat pattern genomic variant and a second repeat pattern genomic variant;
(p) estimating a second expected joint probability distribution of the length of the first repeat pattern and of the length of the second repeat pattern for at least one second genomic variant scenario in the plurality of control data sequence reads;
(q) measuring, read by read, the joint probability distribution for the first repeat pattern and the second repeat pattern in the plurality of patient data sequence reads;
(r) comparing the measured joint probability distribution and the first expected joint probability distribution for the first genomic variant scenario;
(s) comparing the patient joint probability distribution and the second expected joint probability distribution for the second genomic variant scenario;
(t) and selecting the genomic variant scenario characterizing the actual genomic variant scenario for the patient as the scenario which results in the closest comparison.

A possible embodiment of the above proposed methods will now be described and illustrated in the exemplary application of CFTR poly-T/TG genomic variants detection and characterization. FIG. 8 shows an example of an ambiguous variant calling where the mutation may either be interpreted as:
Either FIG. 8a): a single insertion of the TG dinucleotide while in combination with a T→G single nucleotide polymorphism in the poly-T homopolymer region on allele 1, and a double deletion of the TG dinucleotide while no mutations are identified in the poly-T homopolymer region on allele 2. The T→G single nucleotide polymorphism on allele 1 is indeed equivalent to the combination of the joint insertion on the TG repetitive sequence and deletion on the T repetitive sequence. due to the overlap of one nucleotide (T) between the heteropolymer and the homopolymer patterns.
Or FIG. 8b): a double insertion of the TG dinucleotide while no mutations are identified in the poly-T homopolymer region on allele 1, and a double deletion of the TG dinucleotide in combination with a double deletion of the T nucleotide in the poly-T homopolymer region on allele 2.

Figure 10A:
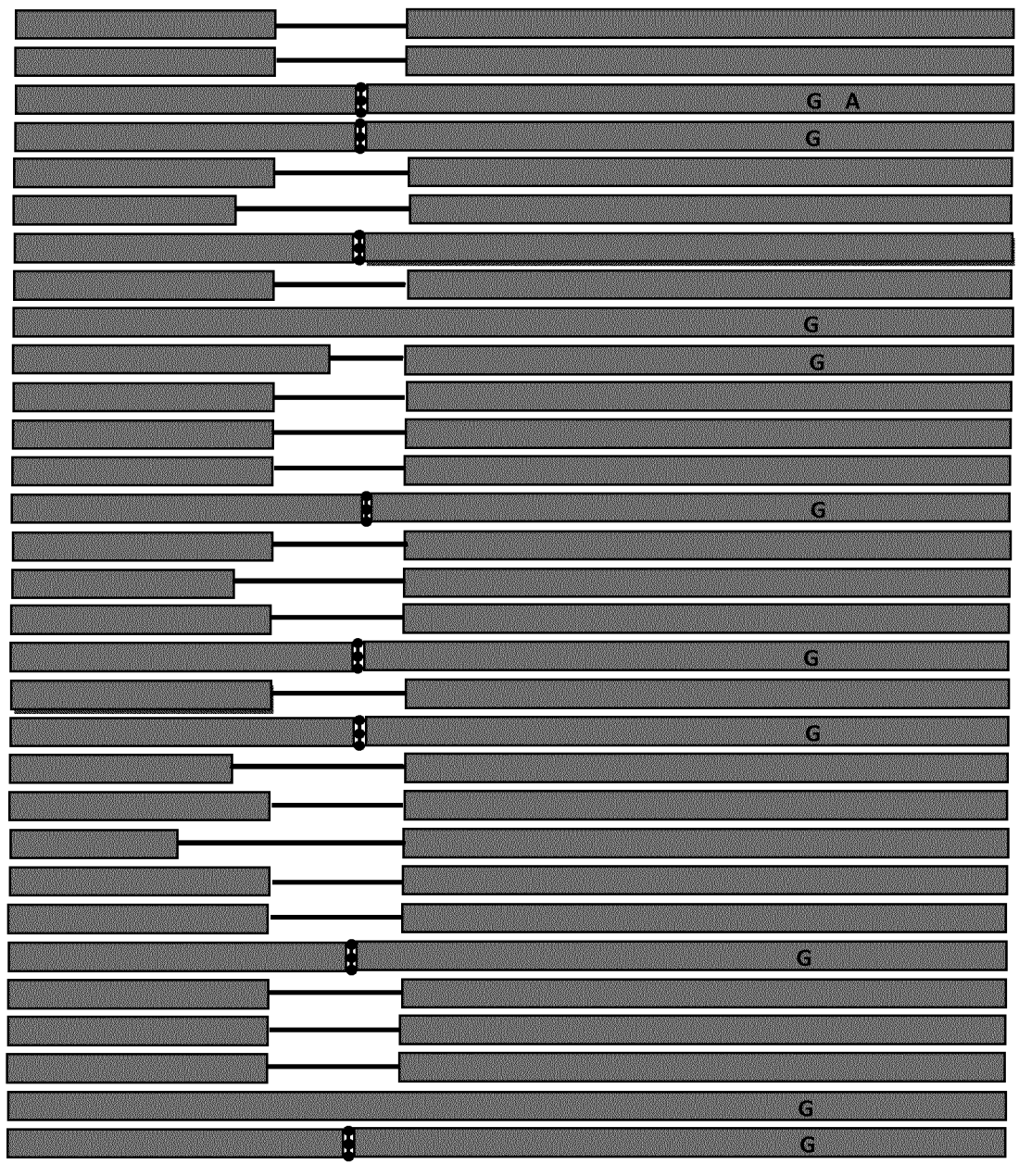
FIG. 10a) shows exemplary reads where the G insertion mutation and the TG deletion mutation most often occur together, on the same reads, while FIG. 10b) shows exemplary reads where the G insertion mutation and the TG deletion mutation most often occur separately, on different reads.

FIG. 9a) and FIG. 9b) show the exemplary joint probability distributions, which can be measured read by read from patient data, for the above scenarios of the ambiguous variant calling, where both the first variant scenario of FIG. 8a) and the second variant scenario of FIG. 8b) provide two peaks of 18% in the measured distribution for all aligned reads. Such variant calling ambiguities may be addressed by an improved variant phasing method, by revisiting each read to jointly search for correlation patterns between the occurrence of the first pattern variants and the second pattern variants, so that it is possible to discriminate between the variants which occur independently and those which occur jointly. For instance in the CFTR gene, on a read by read basis, as illustrated on FIG. 10) which shows the reads side by side for each allele:

FIG. 10a): If the assumed TG-insertion and the TT deletion of FIG. 8a) mainly occur together (on the same reads) then the joint probability distribution of their respective pattern repeat lengths may be mapped to [517] poly-T (heterozygous double deletion of the homopolymer nucleotide) and [1319] poly-TG (heterozygous double insertion of one allele and double deletion on the other allele of the heteropolymer dinucleotide).

Figure 10B:
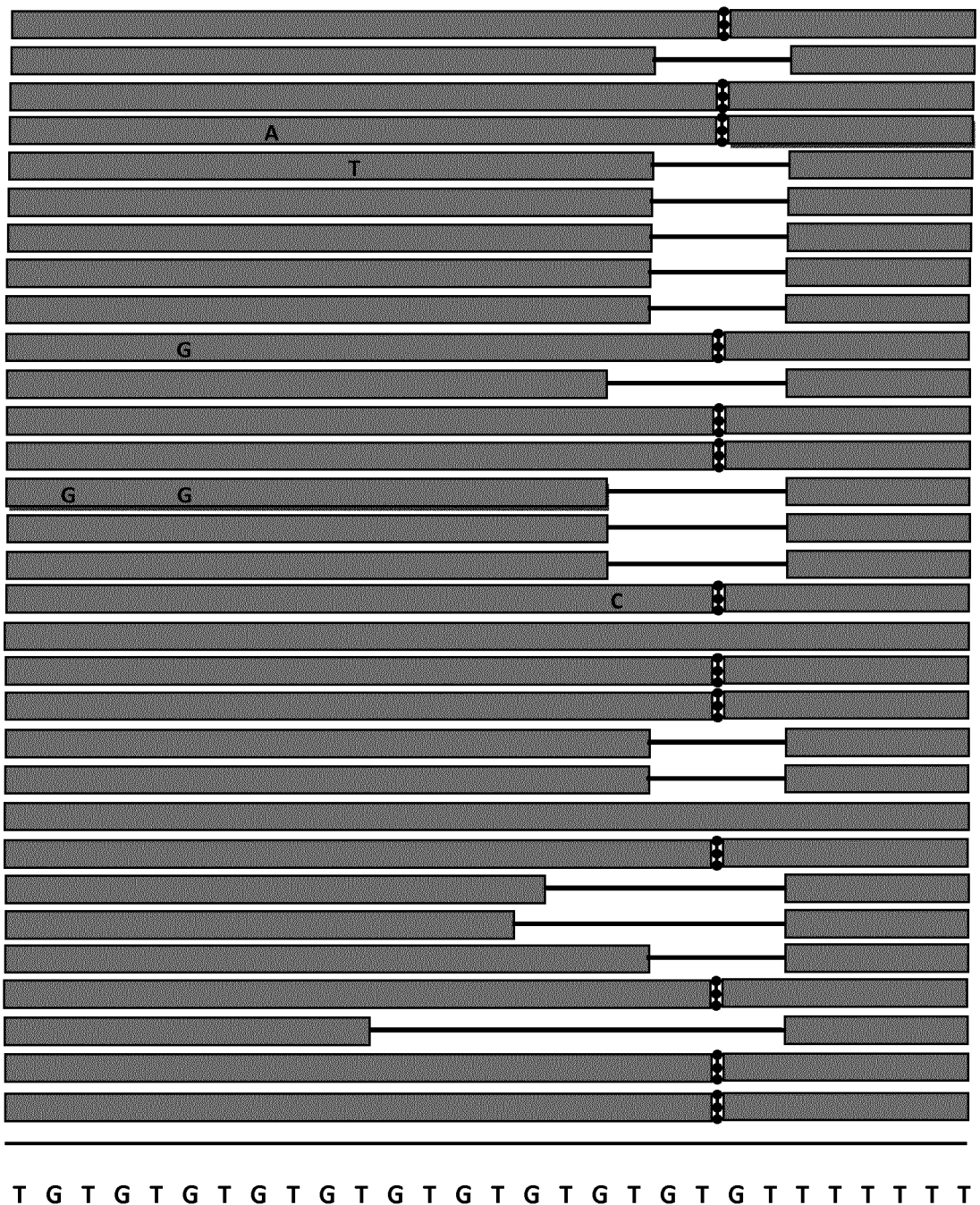

FIG. 10b): If the TG-insertion and the TT deletion of FIG. 8b) mainly occur independently (not on the same reads) then the joint probability distribution of their respective pattern repeat lengths may been mapped to [517] poly-T (heterozygous double deletion of the homopolymer nucleotide) and [9113] poly-TG (heterozygous double deletion of one allele and double insertion on the other allele of the heteropolymer dinucleotide).

Figure 11:
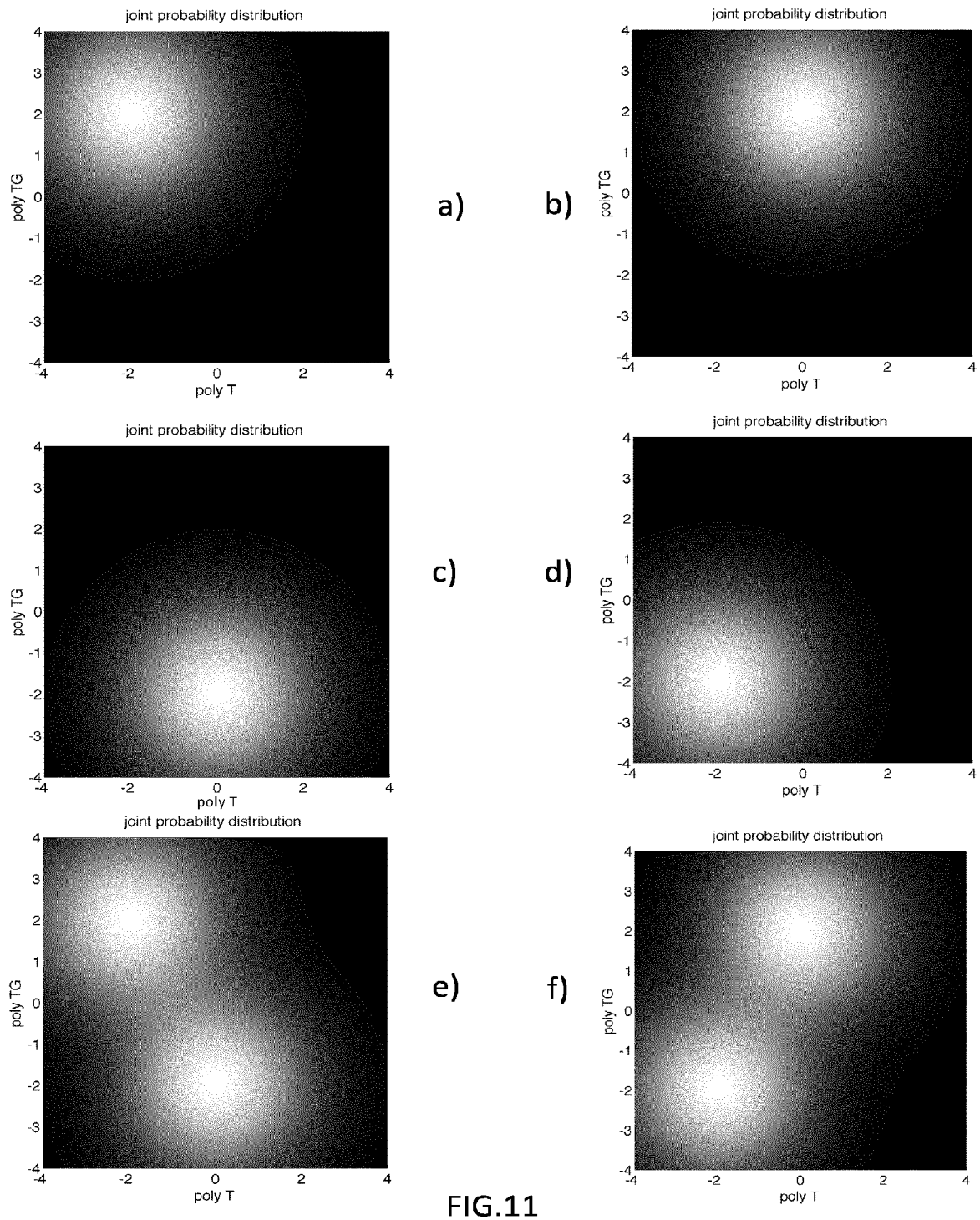
FIG. 11 shows different graphical representation of the joint probability distribution of the relative length of the poly-T first repeat pattern and the relative length of the poly-TG second repeat pattern as may be encountered in a next-generation-sequencing analysis, each different graphical representation a),b),c),d),e),f) representing the joint probability distribution corresponding to a different CFTR gene genomic variant.
Figure 12:
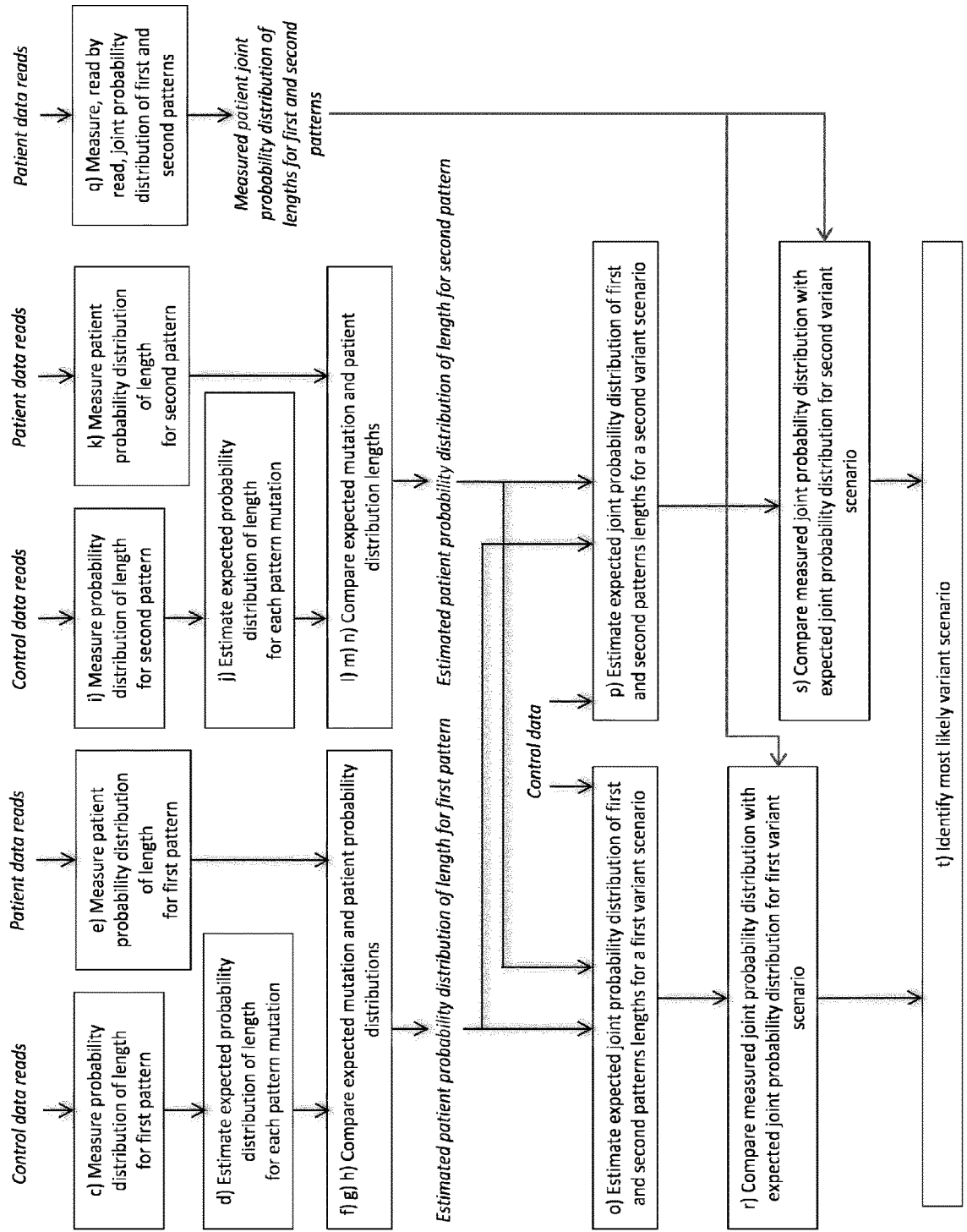
FIG. 12 illustrates a possible workflow of an improved variant calling method according to the present disclosure, which enables to discriminate between ambiguous variants with increased sensitivity and specificity.

FIG. 11 shows the graphical illustration in 2D of a series of joint probability distributions, in relative coordinates, for this example, which can be estimated from the control data, that enables to discriminate between the [517] poly-T combined with [1319] poly-TG first variant scenario (FIG. 8a) from a [517] poly-T combined with [9113] poly-TG second variant scenario (FIG. 8b). FIG. 11a) represents the joint probability distribution for poly-T and poly-TG patterns on allele 1 specifically as estimated for the first scenario variant (two deletions on the poly-T pattern with two insertions on the poly-TG pattern) while FIG. 11b) represents the joint probability distribution for poly-T and poly-TG patterns on allele 1 specifically as estimated for the second variant scenario (no mutation on the poly-T pattern with two insertions on the poly-TG pattern). FIG. 11c) represents the joint probability distribution for poly-T and poly-TG patterns on allele 2 specifically as estimated for the first variant scenario (probability peak at no mutation of the poly-T pattern with two deletions of the poly-TG pattern) while FIG. 11d) represents the joint probability distribution for poly-T and poly-TG patterns on allele 2 specifically as estimated for the second variant scenario (two deletions on the poly-T pattern with two deletions on the poly-TG pattern). FIG. 11e) represents the joint probability distribution for poly-T and poly-TG patterns for both alleles specifically as estimated for the first variant scenario while FIG. 11f) represents the joint probability distribution for poly-T and poly-TG patterns on both alleles specifically as expected for the second variant scenario. As is apparent from the graphical representations of the joint probability distributions in FIG. 11), it is possible to discriminate between the first and second variant scenarios by comparing the measured joint distribution for the poly-T and the poly-TG patterns in the patient data to the expected joint distribution for the poly-T and the poly-TG patterns for each variant respectively. To automatize this phasing, in a possible embodiment, the statistical distance between the measured normalized discrete joint probability distribution of the first and second pattern repeat lengths in the patient data and the expected normalized discrete probability distribution of the first and second pattern repeat lengths for a scenario of i repeats in the first allele and j repeats in the second allele may then be computed as the joint probability L1-L2 Euclidean distance model equation:

$$d = \sqrt{\sum_{l2=0}^{L2} \sum_{l1=0}^{L1} (Po_{l1|l2} - Pe_{l1|l2})^2}$$

where L1 is the maximum repeat length for the first repetitive nucleotide pattern (for instance in the CFTR genomic analysis application, the poly-TG pattern, for which L1=13), and L2 is the maximum repeat length for the second, correlated repetitive nucleotide pattern (for instance in the CFTR genomic analysis application, the poly-T pattern, for which L2=7). $Po_{l1|l2}$ is the measured probability of observing a read with a first repetitive nucleotide pattern of length l1 and a second repetitive nucleotide pattern of length l2 from the patient data, as can be measured read by read, while $Pe_{l1|l2}$ is the expected probability of observing a read with a first repetitive nucleotide pattern of length l1 and a second repetitive nucleotide pattern of length l2, as can be estimated from the control data for a predetermined variant scenario. The distance d between the observed joint probability distribution and the expected joint probability distribution may then be calculated for each possible combination of first repeat pattern and second repeat pattern variants, corresponding to a specific estimated joint probability distribution. The variant scenario for which the minimal value of distance d is calculated may then be selected by the variant calling module 122 as the most likely variant.

The genomic data analyzer 120 may accordingly report 250 detected genomic variants with optimized sensitivity and specificity in response to the sourcing laboratory genomic analysis request. In a possible embodiment the variant calling module 122 outputs the most likely genomic variant scenario. In another possible embodiment, the variant calling module 122 outputs the results for various genomic variants, and the results may be ordered from the most likely to the least likely genomic variant.

The proposed genomic data analyzer 120 enables to serve thousands of sourcing laboratories, processing the data from hundreds of thousands of clinical samples processed with multiple enrichment technologies and sequenced on a diversity of next generation sequencing (NGS) platforms. By utilizing this rich data set coupled with the proposed genomic data analysis methods, robust and accurate variant calling results can be reached with the proposed automated workflow sensitivity and specificity matching that of manual algorithm configuration and fine-tuning by bioinformatics experts. Moreover, the proposed fully automated genomic data analyzer 120 system can be deployed, tested and validated without requiring individual setup and fine-tuning of their specific NGS genomic analysis workflow by the sourcing laboratories, and will thus accelerate access to personalized and precision medicine for hundreds of thousands of patients in Europe and worldwide.

Experimental Data

The proposed genomic data analyzer 120 has been adapted in the Sophia Genetics Data Driven Medicine (DDM) genomic analysis software platform to implement the proposed method as a supplementary method for improved CFTR polyT/TG detection over the prior art NGS workflows. The proposed genomic data analyzer 120 has been operated on a set of genomic samples from Italian patients as part of a new assay experiment, the 188-CF-NGS assay, in comparison with other cystic fibrosis diagnosis methods. As reported by Lucarelli et al in "*A New Targeted CFTR Mutation Panel Based on Next-Generation Sequencing Technology*", The Journal of Molecular Diagnostics, Vol. 19, No. 5, Sep. 2017, one major characteristic of this Italian population is its high genetic heterogeneity of the CFTR gene, which makes it particularly relevant for validation of the proposed method. Two large-scale series of cystic fibrosis patients for central and northern Italy respectively were initially searched for 188 CFTR mutations customized for the Italian population. Overall, 1426 dried blood spots from neonatal screening, 402 genomic DNA samples from various origins, and 1138 genomic DNA samples from patients with CF have been analysed. As an NGS assay reference to detect those mutations, the FDA-approved MiSeqDX Cystic Fibrosis 139-variant assay commercialized by Illumina only reached a detection rate (diagnostic sensitivity) of 86.8% on central Italy samples and 86.9% on Northern Italy samples. It is therefore desirable to customize the analysis of the NGS data reads with the proposed methods in order to further improve the detection rate of complex alleles, which contain more than one mutation and in particular the combination of poly-T and poly-TG tracts. In comparison with this reference assay, the 188-CF-NGS assay reached a significantly improved sensitivity of 95% in central Italy and 95.6% in northern Italy. No false positives were found, thus an overall diagnostic specificity of 100% was reached.

Table 1 lists results of the proposed method to jointly detect T homopolymers and TG heteropolymers in a subset of 24 italian patient samples. The accuracy of the detection has been confirmed for all patient samples for which a Sanger sequencing has also been conducted. Beyond cystic fibrosis diagnosis, preliminary results are currently been collected with the same assay on samples analyzed for other CFTR-related disorders and CBAVD, also showing good performance.

TABLE 1

Results of Sophia DDM detection of polyT/TG variants in a set of 24 italian patient samples, with comparison to Sanger sequencing when available - data for the Multiplicom assay.

| Sample | Sanger Confirmed | DDM Detected |
|---|---|---|
| S1 | poliT 7\|9 | poliT 7\|9 TG 11\|10 |
| S2 | unknown | Reference genome |
| S3 | poliT7\|7 | poliT 7\|7 TG 12\|11 |
| S4 | poliT5\|7-e TG 12\|10 | poliT 5\|7 TG 12\|10 |
| S5 | poliT5\|7 e TG 12\|10 | poliT 5\|7 TG 12\|10 |
| S6 | poliT 7\|7 | poliT 7\|7 TG 11\|10 |
| S7 | unknown | poliT 7\|9 TG 12\|10 |
| S8 | poliT 7\|9 | poliT 7\|9 TG 11\|10 |
| S9 | unknown | Reference genome |
| S10 | unknown | poliT 7\|9 TG 11\|10 |
| S11 | poliT 7\|7 | poliT 7\|7 TG 12\|10 |
| S12 | poliT 7\|7 | poliT 7\|7 TG 11\|9 |
| S13 | unknown | poliT 7\|7 TG 11\|10 |
| S14 | poliT 7\|9 | poliT 7\|9 TG 10\|10 |
| S15 | unknown | Reference genome |
| S16 | poliT 7\|9 | poliT 7\|9 TG 11\|10 |
| S17 | poliT 5\|7 e TG 11\|11 | poliT 5\|7 TG 11\|11 |
| S18 | unknown | poliT 9\|9 TG 10\|10 |
| S19 | unknown | poliT 7\|9 TG 11\|10 |
| S20 | unknown | poliT 7\|7 TG 12\|11 |
| S21 | unknown | Reference genome |
| S22 | unknown | Reference genome |
| S23 | unknown | poliT 7\|7 TG 10\|10 |
| S24 | unknown | poliT 7\|7 TG 11\|10 |

The proposed genomic data analyzer 120 as part of the Sophia Genetics Data Driven Medicine (DDM) genomic analysis software platform has also been validated for use with the Multiplicom (now Agilent) assay CFTR Mastr Dx with drMID Dx for Illumina NGS systems, as detailed in its companion CE-IVD document. A set of 124 independent DNA samples have been analyzed by two independent medical genetic laboratories, each using two independent genomic data analyzers 120 software for data analysis, respectively the SeqNext module v4.1.2 of the Sequence Pilot software as developed by JSI medical systems, Kippenheim, Germany, which does not include the proposed variant calling refinement method 244, and the Sophia DDM application with pipeline ID ILL1MR1G3_CFTR v1 provided by the applicants (Sophia Genetics, Ecublens, Switzerland), adapted to execute the proposed variant calling refinement method 244. This improved Sophia DDM platform thus enables to further analyse the IVS8 polyTG and polyT tracts (reference variants c.1210-34TG(9_13) and c.1210-12T(5_9) located on the human reference genome chromosome 7 'chr7:117188661-117188689', resulting in increased analytical sensitivity, analytical specificity, accuracy, repeatability and reproducibility over the prior art genomic data analyser of JSI medical systems, as shown in Table 2.

TABLE 2

Performance characteristics of the Sophia Genetics DDM genomic analyzer with refined variant calling detection of polyT/TG variants compared to the JSI SeqNext genomic analyzer without refined variant calling detection of polyT/TG variants (experiment conducted with germline DNA extracted from blood samples).

| Parameter | JSI SeqNext | Sophia DDM |
|---|---|---|
| Analytical sensitivity | 100% | 100% |
| Analytical specificity | 99.990% | 100% |
| Accuracy | 99.990% | 100% |
| Repeatability & reproducibility | 99.997% | 100% |

As an alternative to the Multiplicom assay, the proposed genomic data analyzer 120 has also been adapted in the Sophia Genetics Data Driven Medicine (DDM) genomic analysis software platform to implement the proposed method as a supplementary method for improved analysis of the polythymidine variants (5T/7T/9T) along with the upstream TG-repeat region within intron 9 (IVS8) in the Devyser CFTR kit. As can be seen in Table 3, the results of the proposed method to jointly detect T homopolymers and TG heteropolymers in the same subset of 24 italian patient samples have been the same as with the Multiplicom assay in Table 1.

TABLE 3

Results of Sophia DDM detection of polyT/TG variants in a set of 24 italian patient samples, with comparison to Sanger sequencing when available - data for Devyser assay.

| Sample | Sanger Confirmed | DDM Detected |
|---|---|---|
| S1 | poliT 7\|9 | poliT 7\|9 TG 11\|10 |
| S2 | unknown | Reference genome |
| S3 | poliT7\|7 | poliT 7\|7 TG 12\|11 |
| S4 | poliT5\|7-e TG 12\|10 | poliT 5\|7 TG 12\|10 |
| S5 | poliT5\|7 e TG 12\|10 | poliT 5\|7 TG 12\|10 |
| S6 | poliT 7\|7 | poliT 7\|7 TG 11\|10 |
| S7 | unknown | poliT 7\|9 TG 12\|10 |
| S8 | poliT 7\|9 | poliT 7\|9 TG 11\|10 |
| S9 | unknown | Reference genome |
| S10 | unknown | poliT 7\|9 TG 11\|10 |
| S11 | poliT 7\|7 | poliT 7\|7 TG 12\|10 |
| S12 | poliT 7\|7 | poliT 7\|7 TG 11\|9 |
| S13 | unknown | poliT 7\|7 TG 11\|10 |

TABLE 3-continued

Results of Sophia DDM detection of polyT/TG variants in a set of 24 italian patient samples, with comparison to Sanger sequencing when available - data for Devyser assay.

| Sample | Sanger Confirmed | DDM Detected |
|---|---|---|
| S14 | poliT 7\|9 | poliT 7\|9 TG 10\|10 |
| S15 | unknown | Reference genome |
| S16 | poliT 7\|9 | poliT 7\|9 TG 11\|10 |
| S17 | poliT 5\|7 e TG 11\|11 | poliT 5\|7 TG 11\|11 |
| S18 | unknown | poliT 9\|9 TG 10\|10 |
| S19 | unknown | poliT 7\|9 TG 11\|10 |
| S20 | unknown | poliT 7\|7 TG 12\|11 |
| S21 | unknown | Reference genome |
| S22 | unknown | Reference genome |
| S23 | unknown | poliT 7\|7 TG 10\|10 |
| S24 | unknown | poliT 7\|7 TG 11\|10 |

Thus, by optimizing an NGS assay based on a mutation panel with the proposed bioinformatics methods, it is possible to provide improved sensitivity and specificity comparable to the classic methods of Sanger sequencing and multiplex litigation-dependent probe amplification (MLPA) at a significantly lower cost for genomic analysis of the CFTR complex mutations. The proposed methods also improve the performance of the prior art NGS workflows in detecting those mutations. Current applications include diagnostics, neonatal and carrier screening, assisted reproduction and cystic fibrosis genetic counseling.

Other Embodiments and Applications

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In particular, as will be apparent to those skilled in the art of genomics and personalized medicine, the proposed methods are not limited to the specifics of the CFTR gene construct, but may more generally apply to genomic regions comprising a combination of homopolymer repeats and heteropolymer repeats causing ambiguity in calling variants with the prior art next-generation-sequencing genomic analyzer 120 workflows. While there is significant medical information on related variants for the CFTR gene and their association with CFTR-related pathologies, other areas of medical genomics practice are still on-going research in associating genomic analysis of certain gene regions with certain pathologies. The proposed refined variant calling method 244 may thus apply to improve the variant detection in other genomic regions than the CFTR gene, if such regions are characterized by different variant combinations of homopolymer repeats and heteropolymer repeats and associated with different diagnoses by future medical research works. This may be the case for instance in the field of neurological diseases where recent development in genome-edited animal models is accelerating the study of multiple mutations, while there are already known associations between certain heteropolymer repeats and certain diseases, such as for instance the CAG polyglutamine (polyQ) repeat variants in Huntington as well as ataxia diseases.

As will be apparent to those skilled in the art of digital data communications, the methods described herein may be indifferently applied to various data structures such as data files or data streams. The terms "data", "data structures", "data fields", "file", or "stream" may thus be used indifferently throughout this specification.

As will be apparent to those skilled in the art statistics, the methods described herein may be indifferently applied to various statistical methods such as probability representations and statistical measurements. The terms "distribution", "likelihood", "probability" may thus be used indifferently throughout this specification.

Although the detailed description above contains many specific details, these should not be construed as limiting the scope of the embodiments but as merely providing illustrations of some of several embodiments.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, units, or mechanisms. Modules or units may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities.

Although an overview of the inventive subject matter has been described with reference to specific example embodiments, various modifications and changes may be made to these embodiments without departing from the broader spirit and scope of embodiments of the present invention. For example, various embodiments or features thereof may be mixed and matched or made optional by a person of ordinary skill in the art. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are believed to be described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present invention as represented by the appended claims. The specification and drawings are, accordingly, to be regarded in an illustrative rather than a restrictive sense.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method for detecting and characterizing, with a processor, a genomic variant scenario as a combination of at least two genomic sequence variants in poly-T and poly-TG tracts of CFTR gene alleles from a cystic fibrosis patient sample, the method comprising:

(a) obtaining a plurality of patient data sequence reads from an enriched genomic sample of a patient using next generation sequencing, wherein obtaining the enriched genomic sample of the patient comprises targeting and enriching sub-regions of a genomic sample of the patient corresponding to the poly-T and poly-TG tracts of CFTR gene alleles;

(b) obtaining a plurality of control data sequence reads from an enriched genomic control sample using next generation sequencing, wherein obtaining the enriched genomic sample of the control data sequence reads comprises targeting and enriching sub-regions of a genomic control sample corresponding to the poly-T and poly-TG tracts of CFTR gene alleles;

(c) measuring a probability distribution of the length of a poly-TG repeat pattern, in the plurality of control data sequence reads;

(d) for each possible genomic variant of the poly-TG repeat pattern relative to the control data poly-TG repeat pattern, estimating the expected probability distribution of the length of the poly-TG repeat pattern for this genomic variant as a function of this genomic variant and of the measured probability distribution of the length of the poly-TG repeat pattern in the plurality of control data sequence reads;

(e) measuring a patient probability distribution of the length of the poly-TG repeat pattern in the plurality of patient data sequence reads;

(f) comparing the measured patient probability distribution and the expected probability distribution of the length of the poly-TG repeat pattern in the control sample;

(g) for each possible genomic variant of the poly-TG repeat pattern, comparing the measured patient probability distribution and the expected probability distribution of the length of the poly-TG repeat pattern for this genomic variant;

(h) selecting an estimated patient probability distribution of the poly-TG repeat pattern length characterizing a poly-TG genomic sequence variant of the cystic fibrosis patient sample as the expected probability distribution which results in the closest comparison with the measured patient probability distribution;

(i) measuring a probability distribution of the length of a poly-T repeat pattern in the plurality of control data sequence reads as the expected probability distribution length of the poly-T repeat pattern in the control sample;

(j) for each possible genomic variant of the poly-T repeat pattern relative to the control data poly-T repeat pattern, estimating the expected probability distribution of the length of the poly-T repeat pattern for this genomic variant as a function of this genomic variant and of the measured probability distribution of the length of the poly-T repeat pattern in the plurality of control data sequence reads;

(k) measuring a patient probability distribution of the length of the poly-T repeat pattern in the plurality of patient data sequence reads;

(l) comparing the measured patient probability distribution and the expected probability distribution of the poly-T repeat pattern in the control sample;

(m) for each possible genomic variant of the poly-T repeat pattern, comparing the measured patient probability distribution and the expected probability distribution of the length of the poly-T repeat pattern for this genomic variant;

(n) selecting an estimated patient probability distribution of the poly-T repeat pattern length characterizing a poly-T genomic sequence variant of the cystic fibrosis patient sample as the expected probability distribution which results in the closest comparison with the measured patient probability distribution;

(o) estimating a first expected joint probability distribution of the length of the poly-TG repeat pattern and of the length of the poly-T repeat pattern for at least one first genomic variant scenario in the plurality of control data sequence reads, the first genomic variant scenario being characterized by: a first allele of the poly-TG repeat pattern genomic variant selected in step (h) and a first allele of the poly-T repeat pattern genomic variant selected in step (n) are on the same reads, while a second allele of the poly-TG repeat pattern genomic variant selected in step (h) and a second allele of the poly-T repeat pattern genomic variant selected in step (n) are on the same reads;

(p) estimating a second expected joint probability distribution of the length of the poly-TG repeat pattern and of the length of the poly-T repeat pattern for at least one second genomic variant scenario in the plurality of control data sequence reads, the second genomic variant scenario being characterized by: the first allele of the poly-TG repeat pattern genomic variant selected in step (h) and the second allele of the poly-T repeat pattern genomic variant selected in step (n) are on the same reads, while the second allele of the poly-TG repeat pattern genomic variant selected in step (h) and the first allele of the poly-T repeat pattern genomic variant selected in step (n) are on the same reads;

(q) measuring, read by read, the patient joint probability distribution for the length of the poly-TG repeat pattern and the length of the poly-T repeat pattern in the plurality of patient data sequence reads;

(r) comparing the measured patient joint probability distribution and the first expected joint probability distribution for the first genomic variant scenario;

(s) comparing the measured patient joint probability distribution and the second expected joint probability distribution for the second genomic variant scenario; and (t) selecting the genomic variant scenario characterizing the actual genomic variant scenario for the patient as the scenario which results in the closest comparison.

2. The method of claim 1, wherein the genomic variant comprises at least one insertion or one deletion on one allele of the basic motif relative to the repeat pattern of the control data.

3. The method of claim 2, wherein estimating the expected probability distribution of the length of the repeat pattern for each possible genomic variant as a function of the genomic variant and of the measured probability distribution of the length of the repeat pattern in the plurality of control data sequence reads comprises: for each allele, shifting the measured probability distribution of the repeat pattern in the plurality of control data sequence reads if the genomic variant comprises a deletion or an insertion on the allele, and averaging the resulting measured probability distributions from both alleles.

4. The method according to claim 1, further comprising: reporting, with a processor, through a user interface, the selected genomic variant scenario.

5. The method according to claim 1 further comprising: reporting, with a processor, through a user interface, the comparison results for each genomic variant scenario comparison.

6. The method according to claim 1, wherein the measured patient probability distribution of the length is a discrete probability distribution of an absolute length of the repeat nucleotide pattern or a discrete normalized probability distribution of a relative length of the repeat nucleotide relative to a wild type repeat pattern most commonly found without mutation.

7. The method according to claim 6, wherein comparing the measured patient probability distribution with the expected probability distribution in step (g) or in step (m) comprises measuring a mathematical distance between a measured patient normalized discrete probability distribution and an expected normalized discrete probability distribution, and wherein selecting the estimated patient probability distribution characterizing a possible variant of the cystic fibrosis patient sample in step (h) or step (n) comprises selecting the expected probability distribution which results in a lowest distance measurement.

8. The method according to claim 7, wherein a statistical distance between the measured absolute discrete probability distribution of the length in the patient data and the expected absolute discrete probability distribution of the length for a variant scenario of i repeats of a nucleotide pattern in the first allele and j repeats in the second allele is computed as the Euclidean distance:

$$d_{i|j} = \sqrt{\sum_{l=0}^{L}(P_{i|j,l} - P_l)^2}$$

where L is the maximum repeat length, i|j corresponds to the variant of i repeats on the first allele and j repeats on the second allele, $P_l$ is the probability of observing a repeat with exact length l from the patient data, $P_l|j,l$ the probability of observing a repeat with exact length l from the control data, with the distribution shifted by i repeats in the first allele and j repeats in the second allele.

9. The method according to claim 8, wherein the distance $d_{i|j}$ between the expected distribution and the observed patient distribution is calculated for all possible combinations of allele variants i|j, and wherein the estimated patient probability distribution characterizing a possible variant of the cystic fibrosis patient sample is selected in step (h) or (n) as the estimated patient probability distribution which results in a minimum $d_{i|j}$ distance.

10. The method according to claim 1, wherein comparing in step (r) or step (s) the measured patient joint probability distribution with the first expected joint probability distribution or the second expected joint probability distribution, respectively, comprises measuring a distance between a measured normalized discrete joint probability distribution of the poly-TG and the poly-T repeat lengths in the patient data and an expected normalized discrete probability distribution of the poly-TG and the poly-T repeat lengths for a scenario of i repeats in the first allele and j repeats in the second allele, the distance being calculated as the L1-L2 Euclidean distance:

$$d = \sqrt{\sum_{l2=0}^{L2}\sum_{l1=0}^{L1}(Po_{l1|l2} - Pe_{l1|l2})^2}$$

where L1 is the maximum repeat length for the poly-TG repeat pattern, L2 is the maximum repeat length for the poly-T repeat pattern, $Po_{l1|l2}$ is the measured probability of observing a read with a first repetitive nucleotide pattern of length l1 and a second repetitive nucleotide pattern of length l2 from the patient data, as can be measured read by read, while $Pe_{l1|l2}$ is the expected probability of observing a read with a first repetitive nucleotide pattern of length l1 and a second repetitive nucleotide pattern of length l2, as can be estimated from the control data for a predetermined scenario.

11. The method according to claim 10, wherein the distance d between the observed joint probability distribution and the expected joint probability distribution is calculated for each possible combination of the poly-TG repeat pattern and the poly-T repeat pattern corresponding to each scenario and wherein the scenario for which a minimal value of distance d is calculated is selected in step (t) as characterizing the actual genomic variant scenario for the cystic fibrosis patient.

12. The method of claim 1, wherein the method is performed on a genomic data analyzer.

13. The method of claim 1, wherein a genomic analysis software platform is configured to implement the method.

* * * * *